United States Patent
Brauer et al.

(10) Patent No.: US 10,799,453 B2
(45) Date of Patent: Oct. 13, 2020

(54) AMLODIPINE FORMULATIONS

(71) Applicant: Silvergate Pharmaceuticals, Inc., Greenwood Village, CO (US)

(72) Inventors: Scott Brauer, Harrisonville, MO (US); Gerold L. Mosher, Kansas City, MO (US)

(73) Assignee: Silvergate Pharmaceuticals, Inc., Greenwood Village, CO (US)

( * ) Notice: Subject to any disclaimer, the term of this patent is extended or adjusted under 35 U.S.C. 154(b) by 0 days.

(21) Appl. No.: 16/381,575

(22) Filed: Apr. 11, 2019

(65) Prior Publication Data

US 2019/0314279 A1 Oct. 17, 2019

Related U.S. Application Data

(60) Provisional application No. 62/656,188, filed on Apr. 11, 2018.

(51) Int. Cl.
| | |
|---|---|
| *A61K 9/10* | (2006.01) |
| *A61K 31/451* | (2006.01) |
| *A61K 47/26* | (2006.01) |
| *A61K 9/14* | (2006.01) |
| *A61K 47/02* | (2006.01) |
| *A61K 47/38* | (2006.01) |
| *A61K 47/24* | (2006.01) |
| *A61K 47/12* | (2006.01) |

(52) U.S. Cl.
CPC .............. *A61K 9/10* (2013.01); *A61K 9/14* (2013.01); *A61K 31/451* (2013.01); *A61K 47/02* (2013.01); *A61K 47/12* (2013.01); *A61K 47/24* (2013.01); *A61K 47/26* (2013.01); *A61K 47/38* (2013.01)

(58) Field of Classification Search
CPC .......... A61K 9/10; A61K 9/14; A61K 31/451; A61K 47/02; A61K 47/12; A61K 47/26; A61K 47/38
See application file for complete search history.

(56) References Cited

U.S. PATENT DOCUMENTS

| | | | |
|---|---|---|---|
| 4,572,909 A | 2/1986 | Campbell et al. | |
| 4,879,303 A | 11/1989 | Davison et al. | |
| 6,057,344 A | 5/2000 | Young | |
| 6,291,490 B1 | 9/2001 | Young | |
| 6,333,342 B1 | 12/2001 | Foster | |
| 6,448,275 B2 | 9/2002 | Young | |
| 6,451,826 B2 | 9/2002 | Young | |
| 6,479,525 B2 | 11/2002 | Lemmens et al. | |
| 6,518,288 B2 | 2/2003 | Lemmens et al. | |
| 6,538,012 B2 | 3/2003 | Ettema et al. | |
| 6,600,047 B2 | 7/2003 | Benneker et al. | |
| 6,646,131 B2 | 11/2003 | Xitian et al. | |
| 6,653,481 B2 | 11/2003 | Peters et al. | |
| 6,680,334 B2 | 1/2004 | Bentham et al. | |
| 6,822,099 B2 | 11/2004 | Senanayake et al. | |
| 6,846,931 B2 | 1/2005 | Youn et al. | |
| 6,890,944 B2 | 5/2005 | Cho et al. | |
| 6,903,124 B2 | 6/2005 | Cho et al. | |
| 7,015,238 B2 | 3/2006 | Lim et al. | |
| 7,115,638 B2 | 10/2006 | Lemmens et al. | |
| 7,199,247 B2 | 4/2007 | Lemmens et al. | |
| 7,772,400 B2 | 8/2010 | Kim et al. | |
| 8,158,146 B2 | 4/2012 | Kadosh et al. | |
| 8,377,994 B2 | 2/2013 | Gray et al. | |
| 2002/0176889 A1 | 11/2002 | Lemmens et al. | |
| 2003/0199559 A1 | 10/2003 | Benneker et al. | |
| 2005/0019395 A1 | 1/2005 | Pragai et al. | |
| 2006/0030602 A1* | 2/2006 | Laughlin | A61K 31/455 514/356 |
| 2006/0035940 A1* | 2/2006 | Laughlin | A61K 31/455 514/356 |
| 2009/0098200 A1 | 4/2009 | Temtsin et al. | |
| 2011/0212169 A1 | 9/2011 | Bae et al. | |
| 2011/0294860 A1* | 12/2011 | Tatsumi | A61K 9/06 514/356 |
| 2012/0177733 A1 | 7/2012 | Joshi et al. | |
| 2014/0024723 A1 | 1/2014 | Brackhagen et al. | |
| 2018/0098978 A1 | 4/2018 | Brauer et al. | |

FOREIGN PATENT DOCUMENTS

| | | | | |
|---|---|---|---|---|
| CN | 101843615 A | | 9/2010 | |
| CN | 102370965 A | | 3/2012 | |
| WO | WO-02053134 A1 | | 7/2002 | |
| WO | WO-2006059217 A1 | | 6/2006 | |
| WO | WO-2008001341 A1 | * | 1/2008 | ........... A61K 9/0004 |
| WO | WO-2012142815 A1 | | 10/2012 | |

OTHER PUBLICATIONS

Dhapte et al. Advances in hydrotropic solutions: An updated review. St. Petersburg Polytechnical University Journal: Physics and Mathematics, vol. 1, Issue 4, Dec. 2015, pp. 424-435. (Year: 2015).*
Bernard et al. Spectrophotometric method of estimation of Amlodipine besylate using hydrotropic solubilization. Journal of Applied Pharmaceutical Science 01 (09); 2011: 177-180. (Year: 2011).*
Jain et al. Spectrophotometric Method Development and Validation for Quantitative Estimation of Amlodipine Besylate in Bulk Drug and Their Dosage Forms by Using Hydrotropic Agent. Eurasian J. Anal. Chem. 5(3): 212-217, 2010. (Year: 2010).*
Allen. Amlodipine 1 mg/mL Oral Liquid. Cardiovascular. Published Feb. 19, 2014 (4 pgs).
Blowey. Update on the pharmacologic treatment of hypertension in pediatrics. Journal of Clinical Hypertension 14(6), 383-387 (2012).
International Application No. PCT/US2017/055576 International Preliminary Report on Patentability dated Apr. 9, 2019.
International Application No. PCT/US2019/027044 International Search Report and Written Opinion dated Jun. 27, 2019.

(Continued)

*Primary Examiner* — Robert A Wax
*Assistant Examiner* — Olga V. Tcherkasskaya
(74) *Attorney, Agent, or Firm* — Wilson Sonsini Goodrich & Rosati

(57) ABSTRACT

Provided herein are stable amlodipine liquid formulations. Also provided herein are methods of using amlodipine liquid formulations for the treatment of certain diseases including hypertension and Coronary Artery Disease (CAD).

19 Claims, 2 Drawing Sheets

(56) References Cited

OTHER PUBLICATIONS

Meyers et al. Pharmacotherapy Review of Chronic Pediatric Hypertension. Clinical Therapeutics (2011), 33(10), 1331-1356. Database: CAPLUS, DOI:10.1016/j.clinthera.2011.09.003.
Nahata et al.: Stability of Amlodipine Besylate; Research; Journal of the American Pharmaceutical Association; 375-377: 39(3) (1999).
Nunn et al. Formulation of medicines for children. British Journal of Clinical Pharmacology, 59:6, pp. 674-676 (2005).
PCT/US2017/055576 International Search Report and Written Opinion dated Dec. 28, 2017.
Seikaly. Hypertension in children: an update on treatment strategies. Current Opinion in Pediatrics, 19:170-177, 2007.
Standing et al. Paediatric formulations—Getting to the heart of the problem. International Journal of Pharmaceutics (2005), 300(1-2), 56-66. Database: CAPLUS.
U.S. Appl. No. 15/726,901 Final Office Action dated Dec. 21, 2018.
U.S. Appl. No. 15/726,901 Office Action dated May 16, 2019.
U.S. Appl. No. 15/726,901 Office Action dated May 3, 2018.
Van Der Vossen et al. Design and stability study of an oral solution of amlodipine besylate for pediatric patients. European Journal of Pharmaceutical Sciences 92:220-223 (2016).
Rosemont Pharmaceuticals Limited, Yorkdale Industrial Park, Braithwaite Street Leeds, LS11 9XE, United Kingdom, "Pharmaceutical product sheet for Amlodipine 1mg/ml Oral Solution," https://www.medicines.org.uk/emc/medicine/30460 (9 pgs.) (retrieved Sep. 12, 2016).
Extended European Search Report dated Apr. 21, 2020 for EP Application No. 17859269.7.
Final Office Action dated Nov. 15, 2019, for U.S. Appl. No. 15/726,901.
International Search Report and Written Opinion dated Dec. 28, 2017, for PCT/US17/055576.
International Search Report and Written Opinion dated Jun. 27, 2019, for PCT/US19/27044.
Notice of Allowance dated Mar. 27, 2020 for U.S. Appl. No. 15/726,901.

\* cited by examiner

AMLODIPINE FORMULATIONS

CROSS-REFERENCE

This application claims priority to U.S. Provisional Application No. 62/656,188, filed Apr. 11, 2018, which is hereby incorporated by reference in its entirety.

BACKGROUND OF THE INVENTION

Hypertension, or high blood pressure, is a serious health issue in many countries. According to the National Heart Blood and Lung Institute, it is thought that about 1 in 3 adults in the United States alone have hypertension. Left unchecked, hypertension is considered a substantial risk factor for cardiovascular and other diseases including coronary heart disease, myocardial infarction, congestive heart failure, stroke and kidney failure. Hypertension is classified as primary (essential) hypertension or secondary hypertension. Primary hypertension has no known cause and may be related to a number of environmental, lifestyle and genetic factors such as stress, obesity, smoking, inactivity and sodium intake. Secondary hypertension can be caused by drug or surgical interventions or by abnormalities in the renal, cardiovascular or endocrine system.

A number of antihypertensive drugs are available for treating hypertension. Various therapeutic classes of antihypertensive drugs include alpha-adrenergic blockers, beta-adrenergic blockers, calcium-channel blockers, hypotensives, mineralcorticoid antagonists, central alpha-agonists, diuretics and rennin-angiotensin-aldosterone inhibitors which include angiotensin II receptor antagonists (ARB) and angiotensin-converting enzyme (ACE) inhibitors. Angiotensin-converting enzyme (ACE) inhibitors inhibit angiotensin-converting enzyme (ACE), a peptidyl dipeptidase that catalyzes angiotension I to angiotension II, a potent vasoconstrictor involved in regulating blood pressure.

Amlodipine is a calcium channel blocker. It affects the movement of calcium into the cells of the heart and blood vessels. As a result, amlodipine relaxes blood vessels and increases the supply of blood and oxygen to the heart while reducing its workload. The structural formula of amlodipine is as follows:

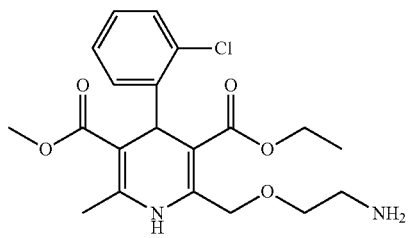 [SMILES: CCOC(=O)C1=C(COCCN)NC(C)=C(C(=O)OC)C1c1ccccc1Cl]

Amlodipine is currently administered in the form of oral tablets, (e.g., amlodipine besylate sold under trademark Norvasc®) or in the form of a refrigerated liquid formulation. In addition to the treatment of hypertension, amlodipine tablets have been used for coronary artery disease (CAD) such as chronic stable angina, vasospastic angina, or angiographically documented coronary artery disease in patients without heart failure or an ejection fraction <40%.

SUMMARY OF THE INVENTION

Disclosed herein is a process for preparing amlodipine benzoate, the process comprising: (i) providing an aqueous mixture comprising an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiment of a process for preparing amlodipine benzoate, the aqueous mixture further comprises a surfactant. In some embodiment of a process for preparing amlodipine benzoate, the surfactant is polysorbate 80. In some embodiment of a process for preparing amlodipine benzoate, the concentration of surfactant is between about 4 mg/ml and about 8 mg/ml. In some embodiment of a process for preparing amlodipine benzoate, the concentration of surfactant is about 6 mg/ml. In some embodiment of a process for preparing amlodipine benzoate, the aqueous mixture is mixed prior to the addition of sodium benzoate in step (ii). In some embodiment of a process for preparing amlodipine benzoate, the amlodipine salt that is more soluble in aqueous media than amlodipine benzoate is amlodipine besylate. In some embodiment of a process for preparing amlodipine benzoate, the concentration of amlodipine besylate is between about 12 mg/ml and about 20 mg/ml. In some embodiment of a process for preparing amlodipine benzoate, the concentration of amlodipine besylate is about 14 mg/ml. In some embodiment of a process for preparing amlodipine benzoate, the concentration of sodium benzoate is between about 40 mg/ml and about 70 mg/ml. In some embodiment of a process for preparing amlodipine benzoate, the concentration of sodium benzoate is about 50 mg/ml. In some embodiment of a process for preparing amlodipine benzoate, the first mixture is mixed before being subjected to ultrasonic agitation. In some embodiment of a process for preparing amlodipine benzoate, the first mixture is mixed while being subjected to ultrasonic agitation. In some embodiment of a process for preparing amlodipine benzoate, the first mixture is mixed after being subjected to ultrasonic agitation. In some embodiment of a process for preparing amlodipine benzoate, the mixing is performed for between about 1 minute and about 30 minutes. In some embodiment of a process for preparing amlodipine benzoate, the mixing is performed for between about 10 minutes and about 30 minutes. In some embodiment of a process for preparing amlodipine benzoate, the frequency of the ultrasonic agitation is between about 20 kHz and about 100 kHz. In some embodiment of a process for preparing amlodipine benzoate, the frequency of the ultrasonic agitation is about 20 kHz. In some embodiment of a process for preparing amlodipine benzoate, the frequency of the ultrasonic agitation is about 40 kHz. In some embodiment of a process for preparing amlodipine benzoate, the duration of the ultrasonic agitation is between about 1 minute and 1 hour. In some embodiment of a process for preparing amlodipine benzoate, the duration of the ultrasonic agitation is between about 5 minutes and 30 minutes. In some embodiment of a process for preparing amlodipine benzoate, the duration of the ultrasonic agitation is between about 5 minutes and 20 minutes. In some embodiment of a process for preparing amlodipine benzoate, the duration of the ultrasonic agitation is about 5 minutes. In some embodiment of a process for preparing amlodipine benzoate, the duration of the ultrasonic agitation is about 10 minutes. In some embodiment of a process for preparing amlodipine benzoate, the temperature of the first mixture or second mixture is not controlled. In some embodiment of a process for preparing amlodipine benzoate, the process does not involve the use of any solvent other than water. The term "D50", as used herein, refers to a particle size in terms of particle diameter in micrometers corresponding to 50% of the volume of the sampled particles being larger than, and 50% of the volume of the sampled particles being smaller than, the recited D50 value. Similarly, the term "D90" refers to a particle size in terms of particle diameter in micrometers corresponding to 90% of the volume of the sampled particles being smaller than, and 10% of the volume of the sampled particles being larger than, the recited D90 value. In some embodiment of a process for preparing amlodipine benzoate, the second mixture comprises amlodipine benzoate particles having a D50 value between about 5 µm and about 20 µm. In some embodiment of a process for preparing amlodipine benzoate, the second mixture comprises amlodipine benzoate particles having a D90 value between about 20 µm and about 40 µm.

Also disclosed herein is a process for preparing an amlodipine benzoate suspension, the process comprising: (i) providing an aqueous mixture comprising an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiment of a process for preparing an amlodipine benzoate suspension, the aqueous mixture further comprises a surfactant. In some embodiment of a process for preparing an amlodipine benzoate suspension, the surfactant is polysorbate 80. In some embodiment of a process for preparing an amlodipine benzoate suspension, the concentration of surfactant is between about 4 mg/ml and about 8 mg/ml. In some embodiment of a process for preparing an amlodipine benzoate suspension, the concentration of surfactant is about 6 mg/ml. In some embodiment of a process for preparing an amlodipine benzoate suspension, the aqueous mixture is mixed prior to the addition of sodium benzoate in step (ii). In some embodiment of a process for preparing an amlodipine benzoate suspension, the amlodipine salt that is more soluble in aqueous media than amlodipine benzoate is amlodipine besylate. In some embodiment of a process for preparing an amlodipine benzoate suspension, the concentration of amlodipine besylate is between about 12 mg/ml and about 20 mg/ml. In some embodiment of a process for preparing an amlodipine benzoate suspension, the concentration of amlodipine besylate is about 14 mg/ml. In some embodiment of a process for preparing an amlodipine benzoate suspension, the concentration of sodium benzoate is between about 40 mg/ml and about 70 mg/ml. In some embodiment of a process for preparing an amlodipine benzoate suspension, the concentration of sodium benzoate is about 50 mg/ml. In some embodiment of a process for preparing an amlodipine benzoate suspension, the first mixture is mixed before being subjected to ultrasonic agitation. In some embodiment of a process for preparing an amlodipine benzoate suspension, the first mixture is mixed while being subjected to ultrasonic agitation. In some embodiment of a process for preparing an amlodipine benzoate suspension, the first mixture is mixed after being subjected to ultrasonic agitation. In some embodiment of a process for preparing an amlodipine benzoate suspension, the mixing is performed for between about 1 minute and about 30 minutes. In some embodiment of a process for preparing an amlodipine benzoate suspension, the mixing is performed for between about 10 minutes and about 30 minutes. In some embodiment of a process for preparing an amlodipine benzoate suspension, the frequency of the ultrasonic agitation is between about 20 kHz and about 100 kHz. In some embodiment of a process for preparing an amlodipine benzoate suspension, the frequency of the ultrasonic agitation is about 20 kHz. In some embodiment of a process for preparing an amlodipine benzoate suspension, the frequency of the ultrasonic agitation is about 40 kHz. In some embodiment of a process for preparing an amlodipine benzoate suspension, the duration of the ultrasonic agitation is between about 1 minute and 1 hour. In some embodiment of a process for preparing an amlodipine benzoate suspension, the duration of the ultrasonic agitation is between about 5 minutes and 30 minutes. In some embodiment of a process for preparing an amlodipine benzoate suspension, the duration of the ultrasonic agitation is between about 5 minutes and 20 minutes. In some embodiment of a process for preparing an amlodipine benzoate suspension, the duration of the ultrasonic agitation is about 5 minutes. In some embodiment of a process for preparing an amlodipine benzoate suspension, the duration of the ultrasonic agitation is about 10 minutes. In some embodiment of a process for preparing an amlodipine benzoate suspension, the temperature of the first mixture or the second mixture is not controlled. In some embodiment of a process for preparing an amlodipine benzoate suspension, the process does not involve the use of any solvent other than water. In some embodiment of a process for preparing an amlodipine benzoate suspension, the process further comprises adding the second mixture comprising amlodipine benzoate to a third mixture comprising one or more of a buffer, a preservative, a sweetening agent, a suspension agent, an antifoaming agent, and a flavoring agent. In some embodiment of a process for preparing an amlodipine benzoate suspension, the process further comprises adding a second surfactant. In some embodiment of a process for preparing an amlodipine benzoate suspension, the second surfactant is added to the second mixture and/or the third mixture. In some embodiment of a process for preparing an amlodipine benzoate suspension, a second surfactant is added to the second mixture. In some embodiment of a process for preparing an amlodipine benzoate suspension, a second surfactant is added to the third mixture. In some embodiment of a process for preparing an amlodipine benzoate suspension, the second surfactant is polysorbate 80. In some embodiment of a process for preparing an amlodipine benzoate suspension, the process further comprises adding water quantum satis thereby forming the amlodipine benzoate suspension. In some embodiment of a process for preparing an amlodipine benzoate suspension, the combined amount of the first surfactant and second surfactant is about 0.1 mg/ml to about 2 mg/ml. In some embodiment of a process for preparing an amlodipine benzoate suspension, the preservative is sodium benzoate, a paraben or paraben salt, or any combinations thereof. In some embodiment of a process for preparing an amlodipine benzoate suspension, the amount of preservative is about 0.1 mg/ml to about 5.0 mg/ml. In some embodiment of a process for preparing an amlodipine benzoate suspension, the buffer comprises a citrate buffer. In some embodiment of a process for preparing an amlodipine benzoate suspension, the citrate buffer concentration is about 3 mM. In some embodiment of a process for preparing an amlodipine benzoate suspension, the suspension agent comprises silicon dioxide, hydroxypropyl methylcellulose, methylcellulose, microcrystalline cellulose, polyvinylpyrrolidone, xanthan gum, magnesium aluminum silicate, crosslinked polyacrylic acid polymers (e.g., the ones sold under the trademark Carbopol®), or any combinations thereof. In some embodiment of a process for preparing an amlodipine benzoate suspension, the suspension agent is silicon dioxide. In some embodiment of a process for preparing an amlodipine benzoate suspension, the amount of silicon dioxide is about 0.1 mg/ml to about 1.0 mg/ml. In some embodiment of a process for preparing an amlodipine benzoate suspension, the suspension agent is hydroxypropyl methylcellulose. In some embodiment of a process for preparing an amlodipine benzoate suspension, the amount of hydroxypropyl methylcellulose is about 3 mg/ml to about 10 mg/ml. In some embodiment of a process for preparing an amlodipine benzoate suspension, the suspension agent is a combination of silicon dioxide and hydroxypropyl methylcellulose. In some embodiment of a process for preparing an amlodipine benzoate suspension, the amount of silicon dioxide is about 0.1 mg/ml to about 1.0 mg/ml and the amount of hydroxypropyl methylcellulose is about 3 mg/ml to about 10 mg/ml. In some embodiment of a process for preparing an amlodipine benzoate suspension, the antifoaming agent is simethicone. In some embodiment of a process for preparing an amlodipine benzoate suspension, the amount of the antifoaming agent is about 0.1 mg/ml to about 1.0 mg/ml. In some embodiment of a process for preparing an amlodipine benzoate suspension, the sweetener is sucralose. In some embodiment of a process for preparing an amlodipine benzoate suspension, the final concentration of amlodipine benzoate in the amlodipine benzoate suspension correspond to about 0.8 mg/ml to about 1.2 mg/ml of amlodipine free base. In some embodiment of a process for preparing an amlodipine benzoate suspension, the amlodipine benzoate suspension comprises amlodipine benzoate particles having a D50 value between about 5 µm and about 40 µm. In some embodiment of a process for preparing an amlodipine benzoate suspension, the amlodipine benzoate suspension comprises amlodipine benzoate particles having a D90 value between about 20 µm and about 60 µm. In some embodiment of a process for preparing an amlodipine benzoate suspension, the pH of the amlodipine benzoate suspension is between about 3 and about 8. In some embodiment of a process for preparing an amlodipine benzoate suspension, the pH is between about 4 and about 5. In some embodiment of a process for preparing an amlodipine benzoate suspension, the pH is between about 5 and about 6. In some embodiment of a process for preparing an amlodipine benzoate suspension, the amlodipine benzoate suspension is stable at about 25±5° C. for at least 12 months. In some embodiment of a process for preparing an amlodipine benzoate suspension, the amlodipine benzoate suspension is stable at about 5±5° C. for at least 12 months. In some embodiment of a process for preparing an amlodipine benzoate suspension, the amlodipine benzoate suspension is stable at about 25±5° C. for at least 24 months. In some embodiment of a process for preparing an amlodipine benzoate suspension, the amlodipine benzoate suspension is stable at about 5±5° C. for at least 24 months.

Also disclosed herein is a process for preparing an amlodipine benzoate suspension, the process comprising: (i) providing an amlodipine besylate aqueous mixture; (ii) adding sodium benzoate to the aqueous mixture to form a first mixture; (iii) subjecting the first mixture to ultrasonic agitation thereby forming a second mixture comprising amlodipine benzoate; and (iv) combining the second mixture with a third mixture comprising sucralose, silicon dioxide, hydroxypropyl methylcellulose, simethicone, a citrate buffer, and optionally a flavoring agent to obtain the amlodipine benzoate suspension; the amlodipine benzoate suspension comprising:
  a) amlodipine benzoate in an amount corresponding to 1.0 mg/ml amlodipine freebase;
  b) about 3 mM of a citrate buffer;
  c) about 0.2 mg/ml to about 5.0 mg/ml of sodium benzoate;
  d) about 0.7 mg/mL sucralose;
  e) about 0.5 mg/ml of silicon dioxide;
  f) about 7.5 mg/ml of hydroxypropyl methylcellulose;
  g) about 0.5 mg/ml simethicone;
  h) about 1.0 mg/ml of polysorbate 80; and
  i) water.

In some embodiment of a process for preparing an amlodipine benzoate suspension, the aqueous mixture further comprises a first portion of polysorbate 80. In some embodiment of a process for preparing an amlodipine benzoate suspension, the concentration of polysorbate 80 in the aqueous mixture is between about 4 mg/ml and about 8 mg/ml. In some embodiment of a process for preparing an amlodipine benzoate suspension, the concentration of polysorbate 80 is about 6 mg/ml. In some embodiment of a process for preparing an amlodipine benzoate suspension, the aqueous mixture is mixed prior to the addition of sodium benzoate in step (ii). In some embodiment of a process for preparing an amlodipine benzoate suspension, the concentration of amlodipine besylate in the aqueous mixture is between about 12 mg/ml and about 20 mg/ml. In some embodiment of a process for preparing an amlodipine benzoate suspension, the concentration of amlodipine besylate in the aqueous mixture is about 14 mg/ml. In some embodiment of a process for preparing an amlodipine benzoate suspension, the concentration of sodium benzoate in the first mixture is between about 40 mg/ml and about 70 mg/ml. In some embodiment of a process for preparing an amlodipine benzoate suspension, the concentration of sodium benzoate in the first mixture is about 50 mg/ml. In some embodiment of a process for preparing an amlodipine benzoate suspension, the first mixture is mixed before being subjected to ultrasonic agitation. In some embodiment of a process for preparing an amlodipine benzoate suspension, the first mixture is mixed while being subjected to ultrasonic agitation. In some embodiment of a process for preparing an amlodipine benzoate suspension, the first mixture is mixed after being subjected to ultrasonic agitation. In some embodiment of a process for preparing an amlodipine benzoate suspension, the mixing is performed for between about 1 minute and about 30 minutes. In some embodiment of a process for preparing an amlodipine benzoate suspension, the mixing is performed for between about 10 minutes and about 30 minutes. In some embodiment of a process for preparing an amlodipine benzoate suspension, the frequency of the ultrasonic agitation is between about 20 kHz and about 100 kHz. In some embodiment of a process for preparing an amlodipine benzoate suspension, the frequency of the ultrasonic agitation is about 20 kHz. In some embodiment of a process for preparing an amlodipine benzoate suspension, the frequency of the ultrasonic agitation is about 40 kHz. In some embodiment of a process for preparing an amlodipine benzoate suspension, the duration of the ultrasonic agitation is between about 1 minute and 1 hour. In some embodiment of a process for preparing an amlodipine benzoate suspension, the duration of the ultrasonic agitation is between about 5 minutes and 30 minutes. In some embodiment of a process for preparing an amlodipine benzoate suspension, the duration of the ultrasonic agitation is between about 5 minutes and 20 minutes. In some embodiment of a process for preparing an amlodipine benzoate suspension, the duration of the ultrasonic agitation is about 5 minutes. In some embodiment of a process for preparing an amlodipine benzoate suspension, the duration of the ultrasonic agitation is about 10 minutes. In some embodiment of a process for preparing an amlodipine benzoate suspension, the temperature of the first mixture or second mixture is not controlled.

In some embodiment of a process for preparing an amlodipine benzoate suspension, the process does not involve the use of any solvent other than water. In some embodiment of a process for preparing an amlodipine benzoate suspension, the process further comprises adding a second portion of polysorbate 80 to the second mixture prior to step (iv). In some embodiment of a process for preparing an amlodipine benzoate suspension, the process further comprises adding water quantum satis thereby forming the amlodipine benzoate suspension. In some embodiment of a process for preparing an amlodipine benzoate suspension, the amlodipine benzoate suspension comprises amlodipine benzoate particles having a D50 value between about 5 μm and about 40 μm. In some embodiment of a process for preparing an amlodipine benzoate suspension, the amlodipine benzoate suspension comprises amlodipine benzoate particles having a D90 value between about 20 μm and about 60 μm. In some embodiment of a process for preparing an amlodipine benzoate suspension, the pH of the amlodipine benzoate suspension is between about 3 and about 8. In some embodiment of a process for preparing an amlodipine benzoate suspension, the pH is between about 4 and about 5. In some embodiment of a process for preparing an amlodipine benzoate suspension, the pH is between about 5 and about 6. In some embodiment of a process for preparing an amlodipine benzoate suspension, the amlodipine benzoate suspension is stable at about 25±5° C. for at least 12 months. In some embodiment of a process for preparing an amlodipine benzoate suspension, the amlodipine benzoate suspension is stable at about 5±5° C. for at least 12 months. In some embodiment of a process for preparing an amlodipine benzoate suspension, the amlodipine benzoate suspension is stable at about 25±5° C. for at least 24 months. In some embodiment of a process for preparing an amlodipine benzoate suspension, the amlodipine benzoate suspension is stable at about 5±5° C. for at least 24 months.

Also disclosed herein is a suspension comprising amlodipine benzoate particles having a D50 value between about 5 μm and about 40 μm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiment of a suspension comprising amlodipine benzoate, the amlodipine benzoate particles have a D50 value between about 10 μm and about 20 μm. In some embodiment of a suspension comprising amlodipine benzoate, the amlodipine benzoate particles have a D90 value between about 20 μm and about 60 μm. In some embodiment of a suspension comprising amlodipine benzoate, the aqueous mixture further comprises a surfactant. In some embodiment of a suspension comprising amlodipine benzoate, the surfactant is polysorbate 80. In some embodiment of a suspension comprising amlodipine benzoate, the concentration of surfactant is between about 4 mg/ml and about 8 mg/ml. In some embodiment of a suspension comprising amlodipine benzoate, the concentration of surfactant is about 6 mg/ml. In some embodiment of a suspension comprising amlodipine benzoate, the aqueous mixture is mixed prior to the addition of sodium benzoate in step (ii). In some embodiment of a suspension comprising amlodipine benzoate, the amlodipine salt that is more soluble in aqueous media than amlodipine benzoate is amlodipine besylate. In some embodiment of a suspension comprising amlodipine benzoate, the concentration of amlodipine besylate is between about 12 mg/ml and about 20 mg/ml. In some embodiment of a suspension comprising amlodipine benzoate, the concentration of amlodipine besylate is about 14 mg/ml. In some embodiment of a suspension comprising amlodipine benzoate, the concentration of sodium benzoate is between about 40 mg/ml and about 70 mg/ml. In some embodiment of a suspension comprising amlodipine benzoate, the concentration of sodium benzoate is about 50 mg/ml. In some embodiment of a suspension comprising amlodipine benzoate, the first mixture is mixed before being subjected to ultrasonic agitation. In some embodiment of a suspension comprising amlodipine benzoate, the first mixture is mixed while being subjected to ultrasonic agitation. In some embodiment of a suspension comprising amlodipine benzoate, the first mixture is mixed after being subjected to ultrasonic agitation. In some embodiment of a suspension comprising amlodipine benzoate, the mixing is performed for between about 1 minute and about 30 minutes. In some embodiment of a suspension comprising amlodipine benzoate, the mixing is performed for between about 10 minutes and about 30 minutes. In some embodiment of a suspension comprising amlodipine benzoate, the frequency of the ultrasonic agitation is between about 20 kHz and about 100 kHz. In some embodiment of a suspension comprising amlodipine benzoate, the frequency of the ultrasonic agitation is about 20 kHz. In some embodiment of a suspension comprising amlodipine benzoate, the frequency of the ultrasonic agitation is about 40 kHz. In some embodiment of a suspension comprising amlodipine benzoate, the duration of the ultrasonic agitation is between about 1 minute and 1 hour. In some embodiment of a suspension comprising amlodipine benzoate, the duration of the ultrasonic agitation is between about 5 minutes and 30 minutes. In some embodiment of a suspension comprising amlodipine benzoate, the duration of the ultrasonic agitation is between about 5 minutes and 20 minutes. In some embodiment of a suspension comprising amlodipine benzoate, the duration of the ultrasonic agitation is about 5 minutes. In some embodiment of a suspension comprising amlodipine benzoate, the duration of the ultrasonic agitation is about 10 minutes. In some embodiment of a suspension comprising amlodipine benzoate, the temperature of the first mixture or the second mixture is not controlled. In some embodiment of a suspension comprising amlodipine benzoate, the process does not involve the use of any solvent other than water. In some embodiment of a suspension comprising amlodipine benzoate, the process further comprises adding the second mixture comprising amlodipine benzoate to a third mixture comprising at least one of a buffer, a preservative, a sweetening agent, a suspension agent, an antifoaming agent, and a flavoring agent. In some embodiment of a suspension comprising amlodipine benzoate, the process further comprises adding a second surfactant. In some embodiment of a suspension comprising amlodipine benzoate, the second surfactant is added to the second mixture and/or the third mixture. In some embodiment of a suspension comprising amlodipine benzoate, the second surfactant is added to the second mixture. In some embodiment of a suspension comprising amlodipine benzoate, the second surfactant is added to the third mixture. In some embodiment of a suspension comprising amlodipine benzoate, the second surfactant is polysorbate 80. In some embodiment of a suspension comprising amlodipine benzoate, the process further comprises adding water quantum satis thereby forming the amlodipine benzoate suspension. In some embodiment of a suspension comprising amlodipine benzoate, the combined amount of the first surfactant and second surfactant is about 0.1 mg/ml to about 2 mg/ml. In some embodiment of a suspension comprising amlodipine benzoate, the preservative is sodium benzoate, a paraben or paraben salt, or any combinations thereof. In some embodiment of a suspension comprising amlodipine benzoate, the amount of preservative is about 0.1 mg/ml to about 5.0 mg/ml. In some embodiment of a suspension comprising amlodipine benzoate, the buffer comprises a citrate buffer. In some embodiment of a suspension comprising amlodipine benzoate, the citrate buffer concentration is about 3 mM. In some embodiment of a suspension comprising amlodipine benzoate, the suspension agent comprises silicon dioxide, hydroxypropyl methylcellulose, methylcellulose, microcrystalline cellulose, polyvinylpyrrolidone, xanthan gum, magnesium aluminum silicate, crosslinked polyacrylic acid polymers (e.g., the ones sold under the trademark Carbopol®), or any combinations thereof. In some embodiment of a suspension comprising amlodipine benzoate, the suspension agent is silicon dioxide. In some embodiment of a suspension comprising amlodipine benzoate, the amount of silicon dioxide is about 0.1 mg/ml to about 1.0 mg/ml. In some embodiment of a suspension comprising amlodipine benzoate, the suspension agent is hydroxypropyl methylcellulose. In some embodiment of a suspension comprising amlodipine benzoate, the amount of hydroxypropyl methylcellulose is about 3 mg/ml to about 10 mg/ml. In some embodiment of a suspension comprising amlodipine benzoate, the suspension agent is a combination of silicon dioxide and hydroxypropyl methylcellulose. In some embodiment of a suspension comprising amlodipine benzoate, the amount of silicon dioxide is about 0.1 mg/ml to about 1.0 mg/ml and the amount of hydroxypropyl methylcellulose is about 3 mg/ml to about 10 mg/ml. In some embodiment of a suspension comprising amlodipine benzoate, the antifoaming agent is simethicone. In some embodiment of a suspension comprising amlodipine benzoate, the amount of the antifoaming agent is about 0.1 mg/ml to about 1.0 mg/ml. In some embodiment of a suspension comprising amlodipine benzoate, the sweetener is sucralose. In some embodiment of a suspension comprising amlodipine benzoate, the final concentration of amlodipine benzoate in the amlodipine benzoate suspension correspond to about 0.8 mg/ml to about 1.2 mg/ml of amlodipine free base. In some embodiment of a suspension comprising amlodipine benzoate, the pH of the amlodipine benzoate suspension is between about 3 and about 8. In some embodiment of a suspension comprising amlodipine benzoate, the pH is between about 4 and about 5. In some embodiment of a suspension comprising amlodipine benzoate, the pH is between about 5 and about 6. In some embodiment of a suspension comprising amlodipine benzoate, the amlodipine benzoate suspension is stable at about 25±5° C. for at least 12 months. In some embodiment of a suspension comprising amlodipine benzoate, the amlodipine benzoate suspension is stable at about 5±5° C. for at least 12 months. In some embodiment of a suspension comprising amlodipine benzoate, the amlodipine benzoate suspension is stable at about 25±5° C. for at least 24 months. In some embodiment of a suspension comprising amlodipine benzoate, the amlodipine benzoate suspension is stable at about 5±5° C. for at least 24 months.

Also disclosed herein is a method of treating hypertension in a subject comprising administering to that subject a therapeutically effective amount of a suspension comprising amlodipine benzoate particles having a D50 value between about 5 μm and about 40 μm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiment of a method of treating hypertension in a subject, the amlodipine benzoate particles have a D50 value between about 10 μm and about 20 μm. In some embodiment of a method of treating hypertension in a subject, the amlodipine benzoate particles have a D90 value between about 20 μm and about 60 μm. In some embodiment of a method of treating hypertension in a subject, the aqueous mixture further comprises a surfactant. In some embodiment of a method of treating hypertension in a subject, the surfactant is polysorbate 80. In some embodiment of a method of treating hypertension in a subject, the concentration of surfactant is between about 4 mg/ml and about 8 mg/ml. In some embodiment of a method of treating hypertension in a subject, the concentration of surfactant is about 6 mg/ml. In some embodiment of a method of treating hypertension in a subject, the aqueous mixture is mixed prior to the addition of sodium benzoate in step (ii). In some embodiment of a method of treating hypertension in a subject, the amlodipine salt that is more soluble in aqueous media than amlodipine benzoate is amlodipine besylate. In some embodiment of a method of treating hypertension in a subject, the concentration of amlodipine besylate is between about 12 mg/ml and about 20 mg/ml. In some embodiment of a method of treating hypertension in a subject, the concentration of amlodipine besylate is about 14 mg/ml. In some embodiment of a method of treating hypertension in a subject, the concentration of sodium benzoate is between about 40 mg/ml and about 70 mg/ml. In some embodiment of a method of treating hypertension in a subject, the concentration of sodium benzoate is about 50 mg/ml. In some embodiment of a method of treating hypertension in a subject, the first mixture is mixed before being subjected to ultrasonic agitation. In some embodiment of a method of treating hypertension in a subject, the first mixture is mixed while being subjected to ultrasonic agitation. In some embodiment of a method of treating hypertension in a subject, the first mixture is mixed after being subjected to ultrasonic agitation. In some embodiment of a method of treating hypertension in a subject, the mixing is performed for between about 1 minute and about 30 minutes. In some embodiment of a method of treating hypertension in a subject, the mixing is performed for between about 10 minutes and about 30 minutes. In some embodiment of a method of treating hypertension in a subject, the frequency of the ultrasonic agitation is between about 20 kHz and about 100 kHz. In some embodiment of a method of treating hypertension in a subject, the frequency of the ultrasonic agitation is about 20 kHz. In some embodiment of a method of treating hypertension in a subject, the frequency of the ultrasonic agitation is about 40 kHz. In some embodiment of a method of treating hypertension in a subject, the duration of the ultrasonic agitation is between about 1 minute and 1 hour. In some embodiment of a method of treating hypertension in a subject, the duration of the ultrasonic agitation is between about 5 minutes and 30 minutes. In some embodiment of a method of treating hypertension in a subject, the duration of the ultrasonic agitation is between about 5 minutes and 20 minutes. In some embodiment of a method of treating hypertension in a subject, the duration of the ultrasonic agitation is about 5 minutes. In some embodiment of a method of treating hypertension in a subject, the duration of the ultrasonic agitation is about 10 minutes. In some embodiment of a method of treating hypertension in a subject, the temperature of the first mixture or the second mixture is not controlled. In some embodiment of a method of treating hypertension in a subject, the process does not involve the use of any solvent other than water. In some embodiment of a method of treating hypertension in a subject, the process further comprises adding the second mixture comprising amlodipine benzoate to a third mixture comprising at least one of a buffer, a preservative, a sweetening agent, a suspension agent, an antifoaming agent, and a flavoring agent. In some embodiment of a method of treating hypertension in a subject, the process further comprises adding a second surfactant. In some embodiment of a method of treating hypertension in a subject, the second surfactant is added to the second mixture and/or the third mixture. In some embodiment of a method of treating hypertension in a subject, the second surfactant is added to the second mixture. In some embodiment of a method of treating hypertension in a subject, the second surfactant is added to the third mixture. In some embodiment of a method of treating hypertension in a subject, the second surfactant is polysorbate 80. In some embodiment of a method of treating hypertension in a subject, the process further comprises adding water quantum satis thereby forming the amlodipine benzoate suspension. In some embodiment of a method of treating hypertension in a subject, the combined amount of the first surfactant and second surfactant is about 0.1 mg/ml to about 2 mg/ml. In some embodiment of a method of treating hypertension in a subject, the preservative is sodium benzoate, a paraben or paraben salt, or any combinations thereof. In some embodiment of a method of treating hypertension in a subject, the amount of preservative is about 0.1 mg/ml to about 5.0 mg/ml. In some embodiment of a method of treating hypertension in a subject, the buffer comprises a citrate buffer. In some embodiment of a method of treating hypertension in a subject, the citrate buffer concentration is about 3 mM. In some embodiment of a method of treating hypertension in a subject, the suspension agent comprises silicon dioxide, hydroxypropyl methylcellulose, methylcellulose, microcrystalline cellulose, polyvinylpyrrolidone, xanthan gum, magnesium aluminum silicate, crosslinked polyacrylic acid polymers (e.g., the ones sold under the trademark Carbopol®), or any combinations thereof. In some embodiment of a method of treating hypertension in a subject, the suspension agent is silicon dioxide. In some embodiment of a method of treating hypertension in a subject, the amount of silicon dioxide is about 0.1 mg/ml to about 1.0 mg/ml. In some embodiment of a method of treating hypertension in a subject, the suspension agent is hydroxypropyl methylcellulose. In some embodiment of a method of treating hypertension in a subject, the amount of hydroxypropyl methylcellulose is about 3 mg/ml to about 10 mg/ml. In some embodiment of a method of treating hypertension in a subject, the suspension agent is a combination of silicon dioxide and hydroxypropyl methylcellulose. In some embodiment of a method of treating hypertension in a subject, the amount of silicon dioxide is about 0.1 mg/ml to about 1.0 mg/ml and the amount of hydroxypropyl methylcellulose is about 3 mg/ml to about 10 mg/ml. In some embodiment of a method of treating hypertension in a subject, the antifoaming agent is simethicone. In some embodiment of a method of treating hypertension in a subject, the amount of the antifoaming agent is about 0.1 mg/ml to about 1.0 mg/ml. In some embodiment of a method of treating hypertension in a subject, the sweetener is sucralose. In some embodiment of a method of treating hypertension in a subject, the final concentration of amlodipine benzoate in the amlodipine benzoate suspension correspond to about 0.8 mg/ml to about 1.2 mg/ml of amlodipine free base. In some embodiment of a method of treating hypertension in a subject, the pH of the amlodipine benzoate suspension is between about 3 and about 8. In some embodiment of a method of treating hypertension in a subject, the pH is between about 4 and about 5. In some embodiment of a method of treating hypertension in a subject, the pH is between about 5 and about 6. In some embodiment of a method of treating hypertension in a subject, the amlodipine benzoate suspension is stable at about 25±5° C. for at least 12 months. In some embodiment of a method of treating hypertension in a subject, the amlodipine benzoate suspension is stable at about 5±5° C. for at least 12 months. In some embodiment of a method of treating hypertension in a subject, the amlodipine benzoate suspension is stable at about 25±5° C. for at least 24 months. In some embodiment of a method of treating hypertension in a subject, the hypertension is primary (essential) hypertension. In some embodiment of a method of treating hypertension in a subject, the hypertension is secondary hypertension. In some embodiment of a method of treating hypertension in a subject, the subject has blood pressure values greater than or equal to 140/90 mmm Hg. In some embodiment of a method of treating hypertension in a subject, the subject is an adult. In some embodiment of a method of treating hypertension in a subject, the subject is elderly. In some embodiment of a method of treating hypertension in a subject, the subject is a child. In some embodiment of a method of treating hypertension in a subject, the suspension is administered to the subject in a fasted state. In some embodiment of a method of treating hypertension in a subject, the suspension is administered to the subject in a fed state. In some embodiment of a method of treating hypertension in a subject, the suspension is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.

Also disclosed herein is a method of treating Coronary Artery Disease (CAD) in a subject comprising administering to that subject a therapeutically effective amount of a suspension comprising amlodipine benzoate particles having a D50 value between about 5 µm and about 40 µm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiment of a method of treating Coronary Artery Disease (CAD) in a subject, the amlodipine benzoate particles have a D50 value between about 10 µm and about 20 µm. In some embodiment of a method of treating Coronary Artery Disease (CAD) in a subject, the amlodipine benzoate particles have a D90 value between about 20 µm and about 60 µm. In some embodiment of a method of treating Coronary Artery Disease (CAD) in a subject, the aqueous mixture further comprises a surfactant. In some embodiment of a method of treating Coronary Artery Disease (CAD) in a subject, the surfactant is polysorbate 80. In some embodiment of a method of treating Coronary Artery Disease (CAD) in a subject, the concentration of surfactant is between about 4 mg/ml and about 8 mg/ml. In some embodiment of a method of treating Coronary Artery Disease (CAD) in a subject, the concentration of surfactant is about 6 mg/ml. In some embodiment of a method of treating Coronary Artery Disease (CAD) in a subject, the aqueous mixture is mixed prior to the addition of sodium benzoate in step (ii). In some embodiment of a method of treating Coronary Artery Disease (CAD) in a subject, the amlodipine salt that is more soluble in aqueous media than amlodipine benzoate is amlodipine besylate. In some embodiment of a method of treating Coronary Artery Disease (CAD) in a subject, the concentration of amlodipine besylate is between about 12 mg/ml and about 20 mg/ml. In some embodiment of a method of treating Coronary Artery Disease (CAD) in a subject, the concentration of amlodipine besylate is about 14 mg/ml. In some embodiment of a method of treating Coronary Artery Disease (CAD) in a subject, the concentration of sodium benzoate is between about 40 mg/ml and about 70 mg/ml. In some embodiment of a method of treating Coronary Artery Disease (CAD) in a subject, the concentration of sodium benzoate is about 50 mg/ml. In some embodiment of a method of treating Coronary Artery Disease (CAD) in a subject, the first mixture is mixed before being subjected to ultrasonic agitation. In some embodiment of a method of treating Coronary Artery Disease (CAD) in a subject, the first mixture is mixed while being subjected to ultrasonic agitation. In some embodiment of a method of treating Coronary Artery Disease (CAD) in a subject, the first mixture is mixed after being subjected to ultrasonic agitation. In some embodiment of a method of treating Coronary Artery Disease (CAD) in a subject, the mixing is performed for between about 1 minute and about 30 minutes. In some embodiment of a method of treating Coronary Artery Disease (CAD) in a subject, the mixing is performed for between about 10 minutes and about 30 minutes. In some embodiment of a method of treating Coronary Artery Disease (CAD) in a subject, the frequency of the ultrasonic agitation is between about 20 kHz and about 100 kHz. In some embodiment of a method of treating Coronary Artery Disease (CAD) in a subject, the frequency of the ultrasonic agitation is about 20 kHz. In some embodiment of a method of treating Coronary Artery Disease (CAD) in a subject, the frequency of the ultrasonic agitation is about 40 kHz. In some embodiment of a method of treating Coronary Artery Disease (CAD) in a subject, the duration of the ultrasonic agitation is between about 1 minute and 1 hour. In some embodiment of a method of treating Coronary Artery Disease (CAD) in a subject, the duration of the ultrasonic agitation is between about 5 minutes and 30 minutes. In some embodiment of a method of treating Coronary Artery Disease (CAD) in a subject, the duration of the ultrasonic agitation is between about 5 minutes and 20 minutes. In some embodiment of a method of treating Coronary Artery Disease (CAD) in a subject, the duration of the ultrasonic agitation is about 5 minutes. In some embodiment of a method of treating Coronary Artery Disease (CAD) in a subject, the duration of the ultrasonic agitation is about 10 minutes. In some embodiment of a method of treating Coronary Artery Disease (CAD) in a subject, the temperature of the first mixture or the second mixture is not controlled. In some embodiment of a method of treating Coronary Artery Disease (CAD) in a subject, the process does not involve the use of any solvent other than water. In some embodiment of a method of treating Coronary Artery Disease (CAD) in a subject, the process further comprises adding the second mixture comprising amlodipine benzoate to a third mixture comprising at least one of a buffer, a preservative, a sweetening agent, a suspension agent, an antifoaming agent, water, and a flavoring agent. In some embodiments, the third mixture comprises water. In some embodiment of a method of treating Coronary Artery Disease (CAD) in a subject, the process further comprises adding a second surfactant. In some embodiment of a method of treating Coronary Artery Disease (CAD) in a subject, the second surfactant is added to the second mixture and/or the third mixture. In some embodiment of a method of treating Coronary Artery Disease (CAD) in a subject, the second surfactant is added to the second mixture. In some embodiment of a method of treating Coronary Artery Disease (CAD) in a subject, the second surfactant is added to the third mixture. In some embodiment of a method of treating Coronary Artery Disease (CAD) in a subject, the second surfactant is polysorbate 80. In some embodiment of a method of treating Coronary Artery Disease (CAD) in a subject, the process further comprises adding water quantum satis thereby forming the amlodipine benzoate suspension. In some embodiment of a method of treating Coronary Artery Disease (CAD) in a subject, the combined amount of the first surfactant and second surfactant is about 0.1 mg/ml to about 2 mg/ml. In some embodiment of a method of treating Coronary Artery Disease (CAD) in a subject, the preservative is sodium benzoate, a paraben or paraben salt, or any combinations thereof. In some embodiment of a method of treating Coronary Artery Disease (CAD) in a subject, the amount of preservative is about 0.1 mg/ml to about 5.0 mg/ml. In some embodiment of a method of treating Coronary Artery Disease (CAD) in a subject, the buffer comprises a citrate buffer. In some embodiment of a method of treating Coronary Artery Disease (CAD) in a subject, the citrate buffer concentration is about 3 mM. In some embodiment of a method of treating Coronary Artery Disease (CAD) in a subject, the suspension agent comprises silicon dioxide, hydroxypropyl methylcellulose, methylcellulose, microcrystalline cellulose, polyvinylpyrrolidone, xanthan gum, magnesium aluminum silicate, crosslinked polyacrylic acid polymers (e.g., the ones sold under the trademark Carbopol®), or any combinations thereof. In some embodiment of a method of treating Coronary Artery Disease (CAD) in a subject, the suspension agent is silicon dioxide. In some embodiment of a method of treating Coronary Artery Disease (CAD) in a subject, the amount of silicon dioxide is about 0.1 mg/ml to about 1.0 mg/ml. In some embodiment of a method of treating Coronary Artery Disease (CAD) in a subject, the suspension agent is hydroxypropyl methylcellulose. In some embodiment of a method of treating Coronary Artery Disease (CAD) in a subject, the amount of hydroxypropyl methylcellulose is about 3 mg/ml to about 10 mg/ml. In some embodiment of a method of treating Coronary Artery Disease (CAD) in a subject, the suspension agent is a combination of silicon dioxide and hydroxypropyl methylcellulose. In some embodiment of a method of treating Coronary Artery Disease (CAD) in a subject, the amount of silicon dioxide is about 0.1 mg/ml to about 1.0 mg/ml and the amount of hydroxypropyl methylcellulose is about 3 mg/ml to about 10 mg/ml. In some embodiment of a method of treating Coronary Artery Disease (CAD) in a subject, the antifoaming agent is simethicone. In some embodiment of a method of treating Coronary Artery Disease (CAD) in a subject, the amount of the antifoaming agent is about 0.1 mg/ml to about 1.0 mg/ml. In some embodiment of a method of treating Coronary Artery Disease (CAD) in a subject, the sweetener is sucralose. In some embodiment of a method of treating Coronary Artery Disease (CAD) in a subject, the final concentration of amlodipine benzoate in the amlodipine benzoate suspension correspond to about 0.8 mg/ml to about 1.2 mg/ml of amlodipine free base. In some embodiment of a method of treating Coronary Artery Disease (CAD) in a subject, the pH of the amlodipine benzoate suspension is between about 3 and about 8. In some embodiment of a method of treating Coronary Artery Disease (CAD) in a subject, the pH is between about 4 and about 5. In some embodiment of a method of treating Coronary Artery Disease (CAD) in a subject, the pH is between about 5 and about 6. In some embodiment of a method of treating Coronary Artery Disease (CAD) in a subject, the amlodipine benzoate suspension is stable at about 25±5° C. for at least 12 months. In some embodiment of a method of treating Coronary Artery Disease (CAD) in a subject, the amlodipine benzoate suspension is stable at about 5±5° C. for at least 12 months. In some embodiment of a method of treating Coronary Artery Disease (CAD) in a subject, the amlodipine benzoate suspension is stable at about 25±5° C. for at least 24 months. In some embodiment of a method of treating Coronary Artery Disease (CAD) in a subject, the Coronary Artery Disease (CAD) is chronic stable angina, vasospastic angina, or angiographically documented coronary artery disease. In some embodiment of a method of treating Coronary Artery Disease (CAD) in a subject, the angiographically documented coronary artery disease is in patients without heart failure or an ejection fraction <40%. In one embodiment of a method of treating Coronary Artery Disease (CAD) in a subject, the suspension is further administered in combination with an additional anti-anginal agent.

In one aspect, disclosed herein is a suspension comprising amlodipine benzoate particles having a D50 value between about 5 μm and about 40 μm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate. In some embodiments, the amlodipine benzoate particles have a D50 value between about 10 μm and about 20 μm. In some embodiments, the amlodipine benzoate particles have a D90 value between about 20 μm and about 60 μm. In some embodiments, the aqueous mixture further comprises a surfactant. In some embodiments, the surfactant is polysorbate 80. In some embodiments, the aqueous mixture is mixed prior to the addition of sodium benzoate in step (ii). In some embodiments, the amlodipine salt that is more soluble in aqueous media than amlodipine benzoate is amlodipine besylate. In some embodiments, the concentration of amlodipine besylate is between about 12 mg/ml and about 20 mg/ml. In some embodiments, the concentration of sodium benzoate is between about 40 mg/ml and about 70 mg/ml. In some embodiments, the first mixture is mixed before, after, or while being subjected to ultrasonic agitation. In some embodiments, the frequency of the ultrasonic agitation is between about 20 kHz and about 100 kHz. In some embodiments, the duration of the ultrasonic agitation is between about 1 minute and 1 hour. In some embodiments, the duration of the ultrasonic agitation is between about 5 minutes and 30 minutes. In some embodiments, the temperature of the first mixture or the second mixture is not controlled. In some embodiments, the process does not involve the use of any solvent other than water. In some embodiments, the process further comprises adding a second surfactant. In some embodiments, the second surfactant is polysorbate 80. In some embodiments, the combined amount of the first surfactant and second surfactant is about 0.1 mg/ml to about 2 mg/ml. In some embodiments, the process further comprises adding the second mixture comprising amlodipine benzoate to a third mixture comprising at least one of a buffer, a preservative, a sweetening agent, a suspension agent, an antifoaming agent, water, and a flavoring agent. In some embodiments, the amount of preservative is about 0.1 mg/ml to about 5.0 mg/ml. In some embodiments, the buffer comprises a citrate buffer. In some embodiments, the citrate buffer concentration is about 3 mM. In some embodiments, the suspension agent comprises silicon dioxide, hydroxypropyl methylcellulose, methylcellulose, microcrystalline cellulose, polyvinylpyrrolidone, xanthan gum, magnesium aluminum silicate, crosslinked polyacrylic acid polymers, or any combinations thereof. In some embodiments, the suspension agent is a combination of silicon dioxide and hydroxypropyl methylcellulose. In some embodiments, the antifoaming agent is simethicone. In some embodiments, the final concentration of amlodipine benzoate in the suspension corresponds to about 0.8 mg/ml to about 1.2 mg/ml of amlodipine free base. In some embodiments, the suspension is stable at about 25±5° C. for at least 6 months. In some embodiments, the suspension is stable at about 5±5° C. for at least 12 months.

In one aspect, disclosed herein is a suspension comprising amlodipine benzoate particles having a D50 value between about 5 μm and about 40 μm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate, wherein the suspension comprises: (a) amlodipine benzoate in an amount corresponding to about 0.8 mg/ml to about 1.2 mg/ml of amlodipine free base; (b) a citrate buffer in an amount between about 1 mM and about 5 mM; (c) about 0.1 mg/ml to about 5.0 mg/ml sodium benzoate; (d) about 0.1 mg/ml to about 1.0 mg/ml of silicon dioxide; (e) about 3 mg/ml to about 10 mg/ml of hydroxypropyl methylcellulose; (f) about 0.1 mg/ml to about 1.0 mg/ml of simethicone; (g) about 0.1 mg/ml to about 2 mg/ml of polysorbate 80; and (h) water.

In one aspect, disclosed herein is a suspension comprising amlodipine benzoate particles having a D50 value between about 5 μm and about 40 μm, the suspension made by the process comprising: (i) providing an aqueous mixture of an amlodipine salt that is more soluble in aqueous media than amlodipine benzoate; (ii) adding sodium benzoate to the aqueous mixture to form a first mixture; and (iii) subjecting the first mixture to ultrasonic agitation thereby forming a second mixture comprising amlodipine benzoate, wherein the suspension comprises: (a) amlodipine benzoate in an amount corresponding to about 1.0 mg/ml of amlodipine free base; (b) about 3 mM of a citrate buffer; (c) about 0.1 mg/ml to about 5.0 mg/ml sodium benzoate; (d) about 0.5 mg/ml of silicon dioxide; (e) about 7.5 mg/ml of hydroxypropyl methylcellulose; (f) about 0.15 mg/ml of simethicone; (g) about 1.0 mg/ml of polysorbate 80; and (h) water, wherein the suspension is stable at about 5±5° C. for at least 12 months.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
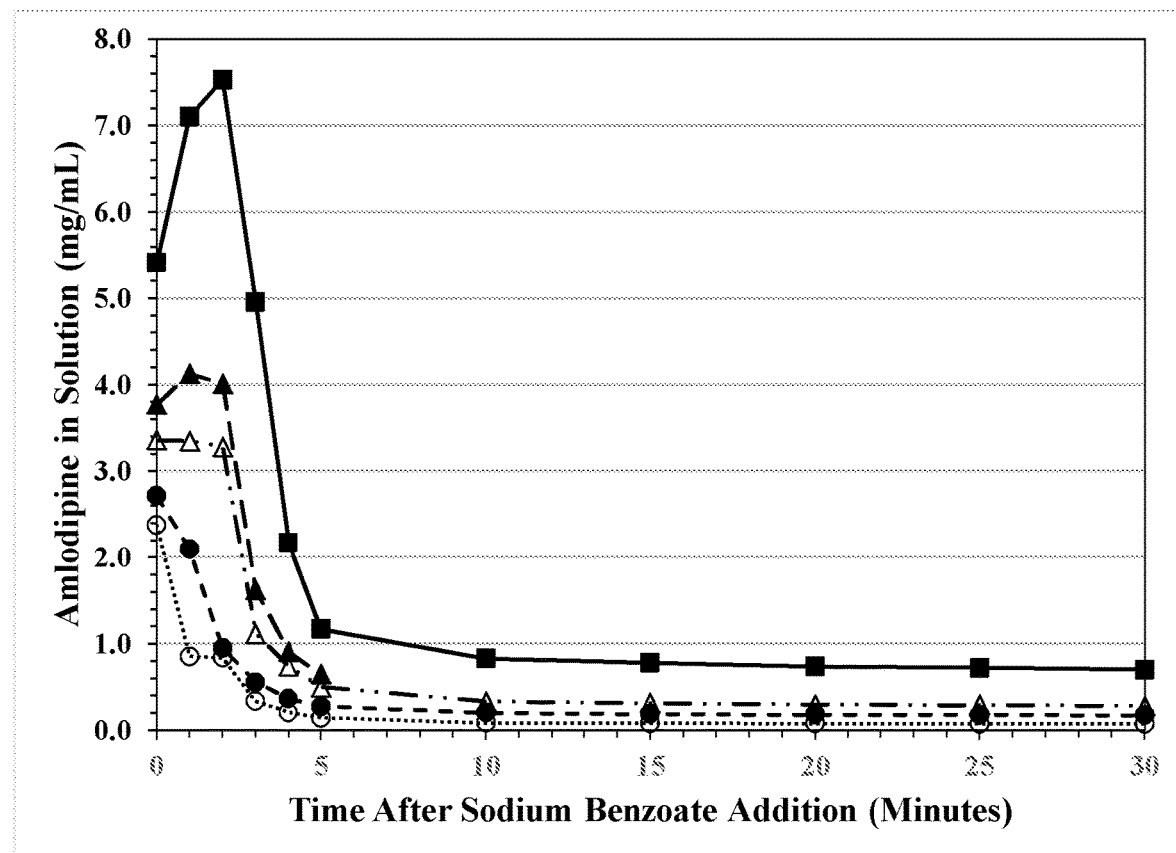
FIG. 1 shows the amount of amlodipine remaining in solution over time in the presence of 1 (○), 3 (•), 5 (Δ), 6 (▲), and 13.3 (■) mg/mL polysorbate 80.

Provided herein are stable amlodipine liquid formulations. These amlodipine formulations described herein are useful for the treatment of hypertension and coronary artery disease. The formulations are advantageous over conventional solid dosage administration of amlodipine ranging from ease of administration, accuracy of dosing, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

Furthermore, the dose of amlodipine to be given to children is calculated according to the child's weight. When the calculated dose is something other than the amount present in one or more intact solid dosage forms, the solid dosage form must be divided to provide the correct dose. This leads to inaccurate dosing when solid dosages forms, such as tablets, are compounded to prepare other formulations for children.

For amlodipine, one solution to overcoming the use of the tablet form is for a compounding pharmacist to pulverize and crush the amlodipine tablet(s) into a powder via mortar and pestle and reconstitute the powder in some liquid form. However, forming a amlodipine oral liquid in this fashion has significant drawbacks including large variability in the actual dosage, incomplete solubilizing of the amlodipine tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or other crushing agent.

The present embodiments described herein provide a safe and effective oral administration of amlodipine for the treatment of hypertension and other disorders. In particular, the embodiments provide stable amlodipine liquid formulations.

As used herein, "amlodipine" refers to amlodipine base, its salt, or solvate or derivative or isomer or polymorph thereof. Suitable compounds include the free base, the organic and inorganic salts, isomers, isomer salts, solvates, polymorphs, complexes etc. U.S. Pat. Nos. 4,572,909, 4,879,303, 6,846,931 and 6,919,087 disclose amlodipine and exemplary amlodipine salt forms. In some embodiments, the amlodipine used in the formulations described herein is a pharmaceutically acceptable amlodipine salt. In some instances, the amlodipine salt is amlodipine benzoate. In other instances, the amlodipine salt is in the form of amlodipine naphthalene sulfonate.

Amlodipine Liquid Formulations

Liquid formulations include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution while other components are in a suspension. In some embodiments, the liquid formulation described herein is a suspension.

In one aspect, the amlodipine liquid formulations described herein comprise a pharmaceutically acceptable salt of amlodipine, a buffer, a preservative, a sweetening agent, a surfactant, a suspension agent, an antifoaming agent, and optionally a flavoring agent. In one embodiment, the buffer is a citrate buffer. In one embodiment, the buffer comprises citric acid. In some embodiments, the buffer further comprises sodium citrate. In one embodiment, the sweetening agent is sucralose. In one embodiment, the sweetening agent is not maltitol. In another embodiment, the sweetening agent is not sucrose. In another embodiment, the preservative is sodium benzoate. In one embodiment, the surfactant is a polysorbate. In some embodiments, the optional surfactant is polysorbate 80. In one embodiment, the suspension agent is silicon dioxide. In some embodiments, the silicon dioxide is colloidal silicon dioxide. In some embodiments, the suspension agent is hydroxypropyl methylcellulose. In some embodiments, the suspension agent is a combination of hydroxypropyl methylcellulose and silicon dioxide. In one embodiment, the antifoaming agent is simethicone.

Pharmaceutically Acceptable Salt of Amlodipine in the Liquid Formulations

Disclosed herein is a stable amlodipine liquid formulation. In some embodiments, the stable amlodipine liquid formulation is in the form of a suspension. In some embodiments, the stable amlodipine liquid formulation comprises a pharmaceutically acceptable salt of amlodipine which is not soluble in an aqueous media.

In some embodiments, the pharmaceutically acceptable salt of amlodipine is amlodipine nicotinate, amlodipine pamoate, amlodipine terephthalate, amlodipine 1-hydroxy-2-naphthoic acid salt, amlodipine (1S)-(+)-10-camphorsulfonic acid salt, or amlodipine 1,5-naphthalene disulfonic acid salt. In some embodiments, the pharmaceutically acceptable salt of amlodipine is amlodipine benzoate or amlodipine naphthalene sulfonate. In some embodiments, the pharmaceutically acceptable salt of amlodipine is amlodipine benzoate. In some embodiments, amlodipine benzoate or amlodipine naphthalene sulfonate are formed in situ. In some embodiments, amlodipine benzoate or amlodipine naphthalene sulfonate are formed by the reaction of a pharmaceutically acceptable salt of amlodipine that is more soluble in aqueous media than amlodipine benzoate or amlodipine naphthalene sulfonate with a molar excess of a salt forming agent. In some embodiments, the pharmaceutically acceptable salt of amlodipine that is more soluble in aqueous media than amlodipine benzoate or amlodipine naphthalene sulfonate is selected from the group consisting of amlodipine besylate, amlodipine tosylate, amlodipine mesylate, amlodipine succinate, amlodipine salicylate, amlodipine maleate, amlodipine acetate, and amlodipine hydrochloride. In some embodiments, the pharmaceutically acceptable salt of amlodipine that is more soluble in aqueous media than amlodipine benzoate or amlodipine naphthalene sulfonate is amlodipine besylate.

In some embodiments, the pharmaceutically acceptable salt of amlodipine is amlodipine benzoate and is formed in situ by the reaction of a pharmaceutically acceptable salt of amlodipine that is more soluble in aqueous media than amlodipine benzoate with a benzoate salt forming agent. In some embodiments, the benzoate salt forming agent is benzoic acid, sodium benzoate, calcium benzoate, or potassium benzoate. In some embodiments, an excess of the benzoate salt forming agent is used to form the benzoate salt in situ. In some embodiments, the benzoate salt forming agent is sodium benzoate. In some embodiments, an excess of sodium benzoate is used to form the benzoate salt in situ. In some embodiments, the amount of sodium benzoate used as the salt forming agent is about 1.0 mg/ml to about 10.0 mg/ml. In some embodiments, the amount of sodium benzoate used as the salt forming agent is about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, or about 10.0 mg/ml.

In some embodiments, the pharmaceutically acceptable salt of amlodipine is amlodipine naphthalene sulfonate and is formed in situ by the reaction of a pharmaceutically acceptable salt of amlodipine that is more soluble in aqueous media than amlodipine naphthalene sulfonate with a naphthalene sulfonate salt forming agent. In some embodiments, the naphthalene sulfonate salt forming agent is 1-naphthalene sulfonic acid, 2-naphthalene sulfonic acid, sodium naphthalene-1-sulfonate, sodium naphthalene-2-sulfonate, or potassium naphthalene-2-sulfonate. In some embodiments, an excess of the naphthalene sulfonate salt forming agent is used to form the naphthalene sulfonate salt in situ. In some embodiments, the naphthalene sulfonate salt forming agent is sodium naphthalene-2-sulfonate. In some embodiments, an excess of sodium naphthalene-2-sulfonate is used to form the naphthalene sulfonate salt in situ. In some embodiments, the amount of sodium naphthalene-2-sulfonate used as the salt forming agent is about 0.5 mg/ml to about 2.5 mg/ml. In some embodiments, the amount of sodium naphthalene-2-sulfonate used as the salt forming agent is about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, or about 2.5 mg/ml.

In some embodiments, the pharmaceutically acceptable salt of amlodipine is formed in situ as a concentrate and is subsequently diluted with water to arrive at the final suspension. In some embodiments, the concentrate is formed in about 5% of the final liquid volume. In some embodiments, the concentrate is formed in about 7.5% of the final liquid volume. In some embodiments, the concentrate is formed in about 10% of the final liquid volume. In some embodiments, the concentrate is formed in about 12.5% of the final liquid volume. In some embodiments, the concentrate is formed in about 15% of the final liquid volume. In some embodiments, the concentrate is formed in about 20% of the final liquid volume. In some embodiments, the concentrate is formed in about 25% of the final liquid volume. In some embodiments, the concentrate is formed in about 30% of the final liquid volume. In some embodiments, the concentrate is formed in about 35% of the final liquid volume. In some embodiments, the concentrate is formed in about 40% of the final liquid volume. In some embodiments, the concentrate is formed in about 45% of the final liquid volume. In some embodiments, the concentrate is formed in about 50% of the final liquid volume. In some embodiments, the concentrate is formed in about 55% of the final liquid volume. In some embodiments, the concentrate is formed in about 60% of the final liquid volume. In some embodiments, the concentrate is formed in about 65% of the final liquid volume. In some embodiments, the concentrate is formed in about 70% of the final liquid volume. In some embodiments, the concentrate is formed in about 75% of the final liquid volume. In some embodiments, the concentrate is formed in about 80% of the final liquid volume. In some embodiments, the concentrate is formed in about 85% of the final liquid volume. In some embodiments, the concentrate is formed in about 90% of the final liquid volume. In some embodiments, the concentrate is formed in about 95% of the final liquid volume.

In some embodiments, the concentration of the pharmaceutically acceptable salt of amlodipine, e.g.; amlodipine benzoate, in the concentrate corresponds to between about 6 mg/ml and about 20 mg/ml of amlodipine free base. In some embodiments, the concentration of the pharmaceutically acceptable salt of amlodipine in the concentrate is about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 10.5 mg/ml, about 11 mg/ml, about 11.5 mg/ml, about 12 mg/ml, about 12.5 mg/ml, about 13 mg/ml, about 13.5 mg/ml, about 14 mg/ml, about 14.5 mg/ml, about 15 mg/ml, about 15.5 mg/ml, about 16 mg/ml, about 16.5 mg/ml, about 17 mg/ml, about 17.5 mg/ml, about 18 mg/ml, about 18.5 mg/ml, about 19 mg/ml, about 19.5 mg/ml, or about 20 mg/ml. In some embodiments, the concentration of the pharmaceutically acceptable salt of amlodipine e.g.; amlodipine benzoate, in the concentrate corresponds to about 6.7 mg/ml of amlodipine free base. In some embodiments, the concentration of the pharmaceutically acceptable salt of amlodipine e.g.; amlodipine benzoate, in the concentrate corresponds to about 10 mg/ml of amlodipine free base. In some embodiments, the concentration of the pharmaceutically acceptable salt of amlodipine e.g.; amlodipine benzoate, in the concentrate corresponds to about 13.5 mg/ml of amlodipine free base. In some embodiments, the concentration of the pharmaceutically acceptable salt of amlodipine e.g.; amlodipine benzoate, in the concentrate corresponds to about 20 mg/ml of amlodipine free base.

In some embodiments, the pharmaceutically acceptable salt of amlodipine is amlodipine benzoate and is formed as a concentrate in situ by the reaction of a pharmaceutically acceptable salt of amlodipine that is more soluble in aqueous media than amlodipine benzoate with sodium benzoate. In some embodiments, the amount of sodium benzoate used as the salt forming agent is between about 30 mg/ml to about 100 mg/ml. In some embodiments, the amount of sodium benzoate used as the salt forming agent is about 40 mg/ml to about 70 mg/ml. In some embodiments, the amount of sodium benzoate used as the salt forming agent is about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 61 mg/ml, about 62 mg/ml, about 63 mg/ml, about 64 mg/ml, about 65 mg/ml, about 66 mg/ml, about 67 mg/ml, about 68 mg/ml, about 69 mg/ml, about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, or about 100 mg/ml.

In some embodiments, the final concentration of the pharmaceutically acceptable salt of amlodipine in the liquid formulation corresponds to about 0.8 mg/ml to about 1.2 mg/ml of amlodipine free base. In other embodiments, the final concentration of the pharmaceutically acceptable salt of amlodipine in the liquid formulation correspond to about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1.0 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml of amlodipine free base. In some embodiments, the final concentration of the pharmaceutically acceptable salt of amlodipine in the liquid formulation corresponds to about 0.9 mg/ml to about 1.1 mg/ml of amlodipine free base. In some embodiments, the final concentration of the pharmaceutically acceptable salt of amlodipine in the liquid formulation corresponds to about 1.0 mg/ml of amlodipine free base. In some embodiments, the pharmaceutically acceptable salt of amlodipine is amlodipine benzoate. In some embodiments, the final concentration of amlodipine benzoate in the liquid formulation corresponds to about 1.0 mg/ml of amlodipine free base. In some embodiments, the pharmaceutically acceptable salt of amlodipine is amlodipine naphthalene sulfonate. In some embodiments, the final concentration of amlodipine naphthalene sulfonate in the liquid formulation corresponds to about 1.0 mg/ml of amlodipine free base.

In some embodiments, the amount of the pharmaceutically acceptable salt of amlodipine corresponds to about 1% w/w to about 16% w/w of the solids in the liquid formulation. In other embodiments, the amount of the pharmaceutically acceptable salt of amlodipine correspond to about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14% w/w, about 14.1% w/w, about 14.2% w/w, about 14.3% w/w, about 14.4% w/w, about 14.5% w/w, about 14.6% w/w, about 14.7% w/w, about 14.8% w/w, about 14.9% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, or about 16% w/w of the solids in the liquid formulation.

Sweetener in the Amlodipine Liquid Formulations

Sweeteners or sweetening agents include any compounds that provide a sweet taste. This includes natural and synthetic sugars, natural and artificial sweeteners, natural extracts and any material that initiates a sweet sensation in a subject. In some embodiments, a solid/powder sweetener is used in the liquid formulation described herein. In other embodiments, a liquid sweetening agent is used in the liquid formulation described herein.

Sweetening agents illustratively include glucose, fructose, sucrose, xylitol, tagatose, sucralose, maltitol, isomaltulose, hydrogenated isomaltulose sold under the trademark Isomalt™ lactitol, sorbitol, erythritol, trehalose, maltodextrin, polydextrose, and the like. Other sweetening agents illustratively include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweetening agents can be used in the form of crude or refined products such as hydrogenated starch hydrolysates, maltitol syrup, high fructose corn syrup, etc., and as branded products, e.g., a combination of propylene glycol, ethyl alcohol, and proprietary artificial flavor sold under the trademark Sweet Am™ liquid by Flavors of North America, a combination of maltodextrin, sorbitol, and fructose sold under the trademark Sweet Am™ powder with Product Code 918.005, a combination of water, propylene glycol, sorbitol, fructose, and proprietary natural and artificial flavor sold under the trademark Sweet Am™ powder with Product Code 918.010 by Flavors of North America, a combination of 1-10% proprietary plant/vegetable extract and 90-99% dextrose sold under the trademark ProSweet™ by Virginia Dare, a maltitol solution sold under the trademark Maltisweet™ by Ingredion, a sorbitol and sorbitol/xylitol solution sold under the trademark Sorbo™ by SPI Polyols, a high fructose corn syrup sold under the trademark Invertose™ by Ingredion, a combination of sucralose and maltodextrin sold under the trademark Rebalance M60 and X60 by Tate and Lyle, and a sugar containing and sugar-free flavored syrups sold under the trademarks Ora-Sweet® and Ora-Sweet-SF®, respectively, by Paddock Laboratories, Inc. Sweetening agents can be used singly or in combinations of two or more. Suitable concentrations of different sweetening agents can be selected based on published information, manufacturers' data sheets and by routine testing.

In some embodiments, the amlodipine liquid formulation described herein comprises a sweetening agent. In some embodiments, the sweetening agent is sucralose. In some embodiments, the sweetening agent is a combination of sucralose and maltodextrin. In some embodiments, the sweetener is not maltitol. In some embodiments, the sweetener is not sucrose.

In some embodiments, the sweetening agent is present in about 0.5 mg/ml to about 0.9 mg/ml in the liquid formulation. In other embodiments, the sweetening agent is present in about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.60 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.70 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.80 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, or about 0.90 mg/ml in the liquid formulation. In some embodiments, the sweetening agent is present in about 0.6 mg/ml to about 0.8 mg/ml in the liquid formulation. In some embodiments, the sweetening agent is sucralose and is present in about 0.7 mg/ml in the liquid formulation.

In some embodiments, the sweetening agent is present in about 1% w/w to about 10% w/w of the solids in the liquid formulation. In some embodiments, the sweetening agent is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w of the solids in the liquid formulation.

Preservative in the Amlodipine Liquid Formulations

Preservatives include anti-microbials, anti-oxidants, and agents that enhance sterility. Exemplary preservatives include ascorbic acid, ascorbyl palmitate, BHA, BHT, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, the amlodipine liquid formulation described herein comprises a preservative.

In some embodiments, the preservative is a paraben, or a mixture of parabens and the sweetener is a sugar (such as, but not limited to glucose, fructose, sucrose, lactose, maltose) or a sugar alcohol (such as, but not limited to xylitol, mannitol, lactitol, maltitol, sorbitol). In some embodiments, the preservative is a paraben, or a mixture of parabens and the sweetener is not a sugar or a sugar alcohol. In some embodiments, the preservative is sodium benzoate.

In some embodiments, the preservative is present in an amount sufficient to provide antimicrobial effectiveness to the amlodipine liquid formulation described herein. In some embodiments, the amount of preservative sufficient to provide antimicrobial effectiveness is between about 0.1 mg/ml and about 5.0 mg/ml. In other embodiments, the amount of preservative sufficient to provide antimicrobial effectiveness is about 0.1 mg/ml, about 0.25 mg/ml, about 0.5 mg/ml, about 0.75 mg/ml, about 1 mg/ml, about 1.25 mg/ml, about 1.5 mg/ml, about 1.75 mg/ml, about 2 mg/ml, about 2.25 mg/ml, about 2.5 mg/ml, about 2.75 mg/ml, about 3 mg/ml, about 3.25 mg/ml, about 3.5 mg/ml, about 3.75 mg/ml, about 4 mg/ml, about 4.25 mg/ml, about 4.5 mg/ml, about 4.75 mg/ml, or about 5 mg/ml.

In some embodiments, the preservative is sodium benzoate and the amount of sodium benzoate sufficient to provide antimicrobial effectiveness is between about 0.2 mg/ml and about 1.0 mg/ml. In some embodiments, the preservative is a paraben and the amount of paraben sufficient to provide antimicrobial effectiveness is between about 1.0 mg/ml and about 3.0 mg/ml. In some embodiments, the preservative is methyl paraben and the amount of methyl paraben sufficient to provide antimicrobial effectiveness is between about 1.0 mg/ml and about 2.0 mg/ml. In some embodiments, the preservative is propyl paraben and the amount of propyl paraben sufficient to provide antimicrobial effectiveness is between about 0.1 mg/ml and about 0.2 mg/ml.

In some embodiments, the preservative is present in about 0.5% w/w to about 15% w/w of the solids in the liquid formulation. In other embodiments, the preservative is present in about 0.5% w/w, about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 11% w/w, about 11.5% w/w, about 12% w/w, about 12.5% w/w, about 13% w/w, about 13.5% w/w, about 14% w/w, about 14.5% w/w, or about 15% w/w of the solids in the liquid formulation.

Sweetener and Preservative Incompatibility

Paraben preservatives (especially methylparaben) can react with selected sugars (glucose, fructose, sucrose, lactose, maltose) and sugar alcohols (xylitol, mannitol, lactitol, maltitol, sorbitol) to form transesterification reaction products. This can be undesirable from a formulation and stability standpoint as the transesterification creates additional degradants.

In some embodiments, the amlodipine liquid formulation described herein does not comprise a paraben preservative. In further embodiments, the amlodipine liquid formulation described herein does not comprise a paraben preservative when the formulation also comprises a sugar or sugar alcohol.

Buffers in the Amlodipine Liquid Formulations

Buffering agents maintain the pH of the liquid amlodipine formulation. Non-limiting examples of buffering agents include, but are not limited to sodium bicarbonate, potassium bicarbonate, magnesium hydroxide, magnesium lactate, magnesium gluconate, aluminum hydroxide, aluminum hydroxide/sodium bicarbonate co-precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartrate, sodium acetate, sodium carbonate, phosphoric acid, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

In some embodiments, the liquid formulation comprises a buffer. In some embodiments, the liquid formulation comprises a citrate buffer. In some embodiments, the buffer in the amlodipine liquid formulation described herein comprises citric acid. In some embodiments, the buffer in the amlodipine liquid formulation described herein comprises citric acid and sodium citrate. In some embodiments, the sodium citrate is monosodium citrate. In some embodiments, the sodium citrate is disodium citrate. In some embodiments, the sodium citrate is trisodium citrate. In some embodiments, the liquid formulation comprises a phosphate buffer. In some embodiments, the buffer in the amlodipine liquid formulation described herein comprises phosphoric acid. In some embodiments, the buffer in the amlodipine liquid formulation described herein comprises phosphoric acid and sodium phosphate. In some embodiments, the buffer in the amlodipine liquid formulation described herein comprises sodium phosphate. In some embodiments, the sodium phosphate is sodium dihydrogen phosphate. In some embodiments, the sodium phosphate is sodium hydrogen phosphate. In some embodiments, the sodium phosphate is trisodium phosphate.

In some embodiments, the pH of the amlodipine liquid formulation described herein is between about 3 and about 8. In some embodiments, the pH of the amlodipine liquid formulation described herein is between about 4 and about 5. In some embodiments, the pH of the amlodipine liquid formulation described herein is between about 5 and about 6. In some embodiments, the pH of the amlodipine liquid formulation described herein is less than about 4, less than about 4.5, less than about 5, less than about 5.5, less than about 6, less than about 6.5, less than about 7, less than about 7.5, or less than about 8. In some embodiments, the pH of the amlodipine liquid formulation described herein is about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8.

In some embodiments, the buffer concentration is between about 1 mM and about 60 mM. In some embodiments, the buffer concentration is about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 10.5 mM, about 11 mM, about 11.5 mM, about 12 mM, about 12.5 mM, about 13 mM, about 13.5 mM, about 14 mM, about 14.5 mM, about 15 mM, about 15.5 mM, about 16 mM, about 16.5 mM, about 17 mM, about 17.5 mM, about 18 mM, about 18.5 mM, about 19 mM, about 19.5 mM, about 20 mM, about 20.5 mM, about 21 mM, about 21.5 mM, about 22 mM, about 22.5 mM, about 23 mM, about 23.5 mM, about 24 mM, about 24.5 mM, about 25 mM, about 25.5 mM, about 26 mM, about 26.5 mM, about 27 mM, about 27.5 mM, about 28 mM, about 28.5 mM, about 29 mM, about 29.5 mM, about 30 mM, about 30.5 mM, about 31 mM, about 31.5 mM, about 32 mM, about 32.5 mM, about 33 mM, about 33.5 mM, about 34 mM, about 34.5 mM, about 35 mM, about 35.5 mM, about 36 mM, about 36.5 mM, about 37 mM, about 37.5 mM, about 38 mM, about 38.5 mM, about 39 mM, about 39.5 mM, about 40 mM, about 40.5 mM, about 41 mM, about 41.5 mM, about 42 mM, about 42.5 mM, about 43 mM, about 43.5 mM, about 44 mM, about 44.5 mM, about 45 mM, about 45.5 mM, about 46 mM, about 46.5 mM, about 47 mM, about 47.5 mM, about 48 mM, about 48.5 mM, about 49 mM, about 49.5 mM, about 50 mM, about 50.5 mM, about 51 mM, about 51.5 mM, about 52 mM, about 52.5 mM, about 53 mM, about 53.5 mM, about 54 mM, about 54.5 mM, about 55 mM, about 55.5 mM, about 56 mM, about 56.5 mM, about 57 mM, about 57.5 mM, about 58 mM, about 58.5 mM, about 59 mM, about 59.5 mM, or about 60 mM. In some embodiments, the buffer concentration is between about 1 mM and about 5 mM, or about 2 mM and about 4 mM. In some embodiments, the buffer concentration is about 3 mM.

In some embodiments, the buffer in the amlodipine liquid formulation described herein comprises citric acid. In some embodiments, citric acid is present in about 0.1 mg/ml to about 1.0 mg/ml in the liquid formulation. In other embodiments, citric acid is present in about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the liquid formulation. In one embodiment, citric acid is present in about 0.31 mg/ml in the liquid formulation. In some embodiments, citric acid is present in about 5.0 mg/ml to about 15 mg/ml in the liquid formulation. In other embodiments, citric acid is present in about 5.0 mg/ml, about 5.5 mg/ml, about 6.0 mg/ml, about 6.5 mg/ml, about 7.0 mg/ml, about 7.5 mg/ml, about 8.0 mg/ml, about 8.5 mg/ml, about 9.0 mg/ml, about 9.5 mg/ml, about 10.0 mg/ml, about 10.5 mg/ml, about 11.0 mg/ml, about 11.5 mg/ml, about 12.0 mg/ml, about 12.5 mg/ml, about 13.0 mg/ml, about 13.5 mg/ml, about 14.0 mg/ml, about 14.5 mg/ml, or about 15.0 mg/ml in the liquid formulation.

In some embodiments, citric acid is present in about 1% w/w to about 45% w/w of the solids in the liquid formulation. In other embodiments, citric acid is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, or about 45% w/w of the solids in the liquid formulation. In some embodiments, citric acid is present in about 1% w/w to about 20% w/w of the solids in the liquid formulation. In some embodiments, citric acid is present in about 1% w/w to about 1.5% w/w of the solids in the liquid formulation.

In some embodiments, the amlodipine liquid formulation further comprises sodium citrate. In some embodiments, sodium citrate is present in about 0.1 mg/ml to about 1.0 mg/ml in the liquid formulation. In other embodiments, sodium citrate is present in the liquid formulation is about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the liquid formulation. In one embodiment, sodium citrate is present in about 0.36 mg/ml in the liquid formulation.

In some embodiments, sodium citrate is present in about 1% w/w to about 20% w/w of the solids in the liquid formulation. In other embodiments, sodium citrate is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w of the solids in the liquid formulation. In some embodiments, sodium citrate is present in about 1% w/w to about 2% w/w of the solids in the liquid formulation.

In other embodiments, sodium citrate is not added to the formulation.

In some embodiments, the buffer in the amlodipine liquid formulation described herein comprises phosphoric acid. In some embodiments, phosphoric acid is present in about 0.1 mg/ml to about 2.0 mg/ml in the liquid formulation. In other embodiments, phosphoric acid is present in about 0.1 mg/ml, about 0.15 mg/ml, about 0.2 mg/ml, about 0.25 mg/ml, about 0.3 mg/ml, about 0.35 mg/ml, 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1.0 mg/ml, about 1.1 mg/ml, about 1.15 mg/ml, about 1.2 mg/ml, about 1.25 mg/ml, about 1.3 mg/ml, about 1.35 mg/ml, about 1.4 mg/ml, about 1.45 mg/ml, about 1.5 mg/ml, about 1.55 mg/ml, about 1.6 mg/mL, about 1.65 mg/mL, about 1.7 mg/ml, about 1.75 mg/ml, about 1.8 mg/ml, about 1.85 mg/ml, about 1.9 mg/ml, about 1.95 mg/ml, or about 2.0 mg/ml in the liquid formulation.

In some embodiments, phosphoric acid is present in about 1% w/w to about 10% w/w of the solids in the liquid formulation. In other embodiments, citric acid is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w of the solids in the liquid formulation.

In some embodiments, the buffer in the amlodipine liquid formulation described herein comprises sodium hydrogen phosphate. In some embodiments, sodium hydrogen phosphate is present in about 0.1 mg/ml to about 1.0 mg/ml in the liquid formulation. In other embodiments, sodium hydrogen phosphate is present in the liquid formulation is about 0.1 mg/mL, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the liquid formulation.

In some embodiments, sodium hydrogen phosphate is present in about 0.5% w/w to about 5% w/w of the solids in the liquid formulation. In other embodiments, sodium hydrogen phosphate is present in about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w of the solids in the liquid formulation.

Suspension Agent in the Amlodipine Liquid Formulations

A suspension agent or dispersion agent is used to prevent the settling of the pharmaceutically acceptable salt of amlodipine in the liquid formulation.

Suitable suspension agents include but are not limited to polymers such as 3-butoxy-2-hydroxypropylhydroxyethylcellulose, acrylamide homo- and copolymers, acrylic acid homo- and copolymer, alginates, carboxymethylcellulose (sodium and other salts), carboxymethylhydroxyethylcellulose, carboxy-vinyl copolymers, cellulose, such as microcrystalline cellulose, combinations of microcrystalline cellulose with carboxymethylcellulose sodium (such as the ones sold under the trademark Avicel® RC-501, RC-581, RC-591, and CL-611), hydrophobically modified hydroxyethylcellulose, hydroxyethylcellulose, hydroxypropyl guar, hydroxypropyl methylcellulose (such as the ones sold under the trademark Benecel K750® or Benecel K1500®), hydroxypropylcellulose, methylcellulose, natural gums and their derivatives, xanthan gum, guar gum, gum Arabic, partially and fully hydrolyzed polyvinyl alcohols, partially neutralized polyacrylic acid, polyalkylene glycol, polysaccharide gums, polyvinylpyrrolidone and derivatives thereof, starch and its derivatives, vinylpyrrolidone homo- and copolymers, water-soluble cellulose ethers, and the mixtures thereof. Other suitable suspension agents include silicon dioxide, silica powder prepared by precipitating water glass (sodium silicate) with sulfuric acid, which is then dried and sold as a fine powder, fumed alumina (made of primary particles which sinter together to form aggregates), clays such as bentonite, laponites, kaolinite, dickite, and nacrite, pyrophylite, talc, vermiculite, sauconite, saponte, nontronite, and montmorillonite, and organically modified montmorillonite clays. In some embodiments, the suspension agent comprises silicon dioxide. In some embodiment, the silicon dioxide is colloidal silicon dioxide.

In some embodiments, the amlodipine liquid formulation described herein comprises a suspension agent. In some embodiments, the suspension agent comprises silicon dioxide, hydroxypropyl methylcellulose, methylcellulose, microcrystalline cellulose, polyvinylpyrrolidone, or combinations thereof. In some embodiments, the suspension agent is silicon dioxide. In some embodiments, the suspension agent is hydroxypropyl methylcellulose. In some embodiments, the suspension agent is a combination of silicon dioxide and hydroxypropyl methylcellulose. In some embodiments, the suspension agent is polyvinylpyrrolidone.

In some embodiments, the suspension agent is present in about 0.1 mg/ml to about 1.0 mg/ml in the liquid formulation. In other embodiments, the suspension agent is present in about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, or about 1.0 mg/ml in the liquid formulation. In some embodiments, the suspension agent is present in about 0.3 mg/ml to about 0.7 mg/ml in the liquid formulation. In some embodiments, the suspension agent is present in about 0.4 mg/ml to about 0.6 mg/ml in the liquid formulation. In some embodiments, the suspension agent is silicon dioxide and is present in about 0.5 mg/ml in the liquid formulation.

In some embodiments, the suspension agent is present in about 3.0 mg/ml to about 10.0 mg/ml in the liquid formulation. In other embodiments, the suspension agent is present in about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, or about 10.0 mg/ml in the liquid formulation. In some embodiments, the suspension agent is present in about 4.0 mg/ml to about 6.0 mg/ml in the liquid formulation. In some embodiments, the suspension agent is present in about 6.0 mg/ml to about 8.0 mg/ml in the liquid formulation. In some embodiments, the suspension agent is hydroxypropyl methylcellulose and is present in about 5.0 mg/ml in the liquid formulation. In some embodiments, the suspension agent is hydroxypropyl methylcellulose and is present in about 7.5 mg/ml in the liquid formulation. In some embodiments, the suspension agent is hydroxypropyl methylcellulose and is present in about 10 mg/ml in the liquid formulation.

In some embodiments, the suspension agent is present in about 10 mg/ml to about 30 mg/ml in the liquid formulation. In other embodiments, the suspension agent is present in about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml in the liquid formulation. In some embodiments, the suspension agent is polyvinylpyrrolidone and is present in about 10 mg/ml in the liquid formulation. In some embodiments, the suspension agent is polyvinylpyrrolidone and is present in about 20 mg/ml in the liquid formulation. In some embodiments, the suspension agent is polyvinylpyrrolidone and is present in about 30 mg/ml in the liquid formulation.

In some embodiments, the suspension agent is present in about 5 mg/ml to about 15 mg/ml in the liquid formulation. In other embodiments, the suspension agent is present in about 5.0 mg/ml, about 5.5 mg/ml, about 6.0 mg/ml, about 6.5 mg/ml, about 7.0 mg/ml, about 7.5 mg/ml, about 8 mg/ml, about 8.5 mg/ml, about 9 mg/ml, about 9.5 mg/ml, about 10 mg/ml, about 10.5 mg/ml, about 11 mg/ml, about 11.5 mg/ml, about 12 mg/ml, about 12.5 mg/ml, about 13 mg/ml, about 13.5 mg/ml, about 14 mg/ml, about 14.5 mg/ml, or about 15 mg/ml in the liquid formulation. In some embodiments, the suspension agent is a combination of microcrystalline cellulose with carboxymethylcellulose sodium sold under the trademark Avicel® RC-591 and is present in about 5 mg/ml in the liquid formulation. In some embodiments, the suspension agent is a combination of microcrystalline cellulose with carboxymethylcellulose sodium sold under the trademark Avicel® RC-591 and is present in about 7.5 mg/ml in the liquid formulation. In some embodiments, the suspension agent is a combination of microcrystalline cellulose with carboxymethylcellulose sodium sold under the trademark Avicel® RC-591 and is present in about 10 mg/ml in the liquid formulation. In some embodiments, the suspension agent is a combination of microcrystalline cellulose with carboxymethylcellulose sodium sold under the trademark Avicel® RC-591 and is present in about 15 mg/ml in the liquid formulation.

In some embodiments, the suspension agent is present in about 0.4% w/w to about 6% w/w of the solids in the liquid formulation. In other embodiments, the suspension agent is present in about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, or about 6% w/w of the solids in the liquid formulation.

In some embodiments, the suspension agent is present in about 20% w/w to about 50% w/w of the solids in the liquid formulation. In other embodiments, the suspension agent is present in about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, about 40% w/w, about 41% w/w, about 41.5% w/w, about 42% w/w, about 42.5% w/w, about 43% w/w, about 43.5% w/w, about 44% w/w, about 44.5% w/w, about 45% w/w, about 45.5% w/w, about 46% w/w, about 46.5% w/w, about 47% w/w, about 47.5% w/w, about 48% w/w, about 48.5% w/w, about 49% w/w, about 39.5% w/w, or about 50% w/w of the solids in the liquid formulation.

In some embodiments, the suspension agent is present in about 40% w/w to about 85% w/w of the solids in the liquid formulation. In other embodiments, the suspension agent is present in about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, or about 85% w/w of the solids in the liquid formulation.

In some embodiments, the suspension agent is present in about 35% w/w to about 55% w/w of the solids in the liquid formulation. In other embodiments, the suspension agent is present in about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, or about 55% w/w of the solids in the liquid formulation.

Antifoaming Agent in the Amlodipine Liquid Formulations

Antifoaming agents are chemical additives that reduce and hinder the formation of foam in the preparation of liquid formulations. The terms antifoaming agent and defoamer are often used interchangeably. Commonly used agents are insoluble oils, polydimethylsiloxanes (e.g., simethicone) and other silicones, certain alcohols, stearates and glycols. Simethicone is available as a pure material (100° 4) and in combination with other excipients to facilitate dispersion and handling. Common simethicone containing products include a 30% w/w simethicone solid sold under the trademark NuSil MED-342, 100% simethicone liquids sold under the trademark NuSil Med-340, Med-346, and Med-347, 30% simethicone emulsions sold under the trademark Dow Corning® Q7-2587, 7-9245, and Medical Antifoam C. The additive is used to prevent formation of foam or is added to break foam already formed. Antifoaming agents reduce foaming in the preparation of liquid formulations which can result in coagulation of aqueous dispersions.

In some embodiments, the amlodipine liquid formulation described herein comprises an antifoaming agent. In some embodiments, the antifoaming agent is simethicone.

In some embodiments, the antifoaming agent is present in about 0.05 mg/ml to about 1.0 mg/ml in the liquid formulation. In some embodiments, the antifoaming agent is present in about 0.05 mg/ml to about 2.0 mg/ml in the liquid formulation. In some embodiments, the antifoaming agent is present in about 0.05 mg/ml to about 2.5 mg/ml in the liquid formulation. In other embodiments, the antifoaming agent is present in about 0.05 mg/ml, about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1.0 mg/ml, about 1.1 mg/ml, about 1.15 mg/ml, about 1.2 mg/ml, about 1.25 mg/ml, about 1.3 mg/ml, about 1.35 mg/ml, about 1.4 mg/ml, about 1.45 mg/ml, about 1.5 mg/ml, about 1.55 mg/ml, about 1.6 mg/ml, about 1.65 mg/ml, about 1.7 mg/ml, about 1.75 mg/ml, about 1.8 mg/ml, about 1.85 mg/ml, about 1.9 mg/ml, about 1.95 mg/ml, about 2.0 mg/ml, about 2.05 mg/ml, about 2.1 mg/ml, about 2.15 mg/ml, about 2.2 mg/ml, about 2.25 mg/ml, about 2.3 mg/ml, about 2.35 mg/ml, about 2.4 mg/ml, about 2.45 mg/ml, or about 2.5 mg/ml in the liquid formulation. In other embodiments, the antifoaming agent is present in about 0.6 mg/ml in the liquid formulation. In other embodiments, the antifoaming agent is present in about 2.0 mg/ml in the liquid formulation. In some embodiments, the antifoaming agent is present in about 0.05 mg/ml to about 0.3 mg/ml in the liquid formulation. In some embodiments, the antifoaming agent is present in about 0.1 mg/ml to about 0.2 mg/ml in the liquid formulation. In some embodiments, the antifoaming agent is simethicone and is present in about 0.15 mg/ml in the liquid formulation.

In some embodiments, the antifoaming agent is present in about 0.1% w/w to about 7% w/w of the solids in the liquid formulation. In other embodiments, the antifoaming agent is present in about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, or about 7% w/w of the solids in the liquid formulation.

Surfactants in the Amlodipine Liquid Formulations

Surfactants are compounds that lower the surface tension (or interfacial tension) between two liquids or between a liquid and a solid. Most commonly, surfactants are classified according to polar head group. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic. Anionic surfactants contain anionic functional groups at their head, such as sulfate, sulfonate, phosphate, and carboxylates. Prominent alkyl sulfates include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate. Others include: docusate (dioctyl sodium sulfosuccinate), perfluorooctanesulfonate (PFOS), perfluorobutanesulfonate, alkylaryl ether phosphates, alkyl ether phosphates. Cationic surfactant include pH-dependent primary, secondary, or tertiary amines such as octenidine dihydrochloride; and permanently charged quaternary ammonium salts such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Zwitterionic (amphoteric) surfactants have both cationic and anionic centers attached to the same molecule. The cationic part is based on primary, secondary, or tertiary amines or quaternary ammonium cations. The anionic part can be more variable and include sulfonates, as in the sultaines CHAPS (3-[(3-cholamidopropyl)dimethylammonio]-1-propanesulfonate) and cocamidopropyl hydroxysultaine. Betaines such as cocamidopropyl betaine have a carboxylate with the ammonium. The most common biological zwitterionic surfactants have a phosphate anion with an amine or ammonium, such as the phospholipids phosphatidylserine, phosphatidylethanolamine, phosphatidylcholine, and sphingomyelins. Nonionic surfactants include fatty alcohols, cetyl alcohol, stearyl alcohol, and cetostearyl alcohol, and oleyl alcohol. Also used as nonionic surfactants are polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), and polyethoxylated tallow amine (POEA). The most commonly used surfactants are fatty acid esters of sorbitan polyethoxylates, i.e. polysorbate 20 and polysorbate 80. The two differ only in the length of the aliphatic chain that imparts hydrophobic character to the molecules, C-12 and C-18, respectively. Polysorbate 80 is more surface-active and has a lower critical micellar concentration than polysorbate 20.

In some embodiments, the amlodipine liquid formulation described herein comprises a surfactant. In some embodiments, the surfactant is polysorbate 80.

In some embodiments, the surfactant is added to the amlodipine liquid formulation in separate portions during the process for preparing the amlodipine liquid formulation.

In some embodiments, the amlodipine benzoate liquid formulation is prepared by a process comprising: (i) providing an aqueous mixture comprising an amlodipine salt that is more soluble in aqueous media than amlodipine benzoate (e.g., amlodipine besylate); (ii) adding a salt forming agent (e.g., sodium benzoate or benzoic acid) to the aqueous mixture to form a first mixture; and (iii) subjecting the first mixture to ultrasonic agitation thereby forming a second mixture comprising amlodipine benzoate. In some embodiments, the process further comprises adding the second mixture comprising amlodipine benzoate to a third mixture comprising one or more of a buffer, a preservative, a sweetening agent, a suspension agent, an antifoaming agent, water, and a flavoring agent. In some embodiments, the third mixture comprises water.

In some embodiments, the surfactant is added in two separate portions. In some embodiments, a first surfactant portion is added during the formation of the pharmaceutically acceptable salt of amlodipine, e.g., amlodipine benzoate. In some embodiments, a first surfactant portion is added to the water prior to the formation of the aqueous mixture comprising an amlodipine salt that is more soluble in aqueous media than amlodipine benzoate (e.g., amlodipine besylate). In some embodiments, a first surfactant portion is added to the aqueous mixture comprising an amlodipine salt that is more soluble in aqueous media than amlodipine benzoate (e.g., amlodipine besylate) prior to the addition of the salt forming agent (e.g., sodium benzoate or benzoic acid). In some embodiments, a second surfactant portion is added to the second mixture prior to the addition to the third mixture. In some embodiments, a second surfactant portion is added to the third mixture.

In some embodiments, the surfactant is present in about 0.1 mg/ml to about 3.0 mg/ml in the final liquid formulation. In other embodiments, the surfactant is present in about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1.0 mg/ml, about 1.1 mg/ml, about 1.15 mg/ml, about 1.2 mg/ml, about 1.25 mg/ml, about 1.3 mg/ml, about 1.35 mg/ml, about 1.4 mg/ml, about 1.45 mg/ml, about 1.5 mg/ml, about 1.55 mg/ml, about 1.6 mg/ml, about 1.65 mg/ml, about 1.7 mg/ml, about 1.75 mg/ml, about 1.8 mg/ml, about 1.85 mg/ml, about 1.9 mg/ml, about 1.95 mg/ml, about 2.0 mg/ml, about 2.1 mg/ml, about 2.15 mg/ml, about 2.2 mg/ml, about 2.25 mg/ml, about 2.3 mg/ml, about 2.35 mg/ml, about 2.4 mg/ml, about 2.45 mg/ml, about 2.5 mg/ml, about 2.55 mg/ml, about 2.6 mg/ml, about 2.65 mg/ml, about 2.7 mg/ml, about 2.75 mg/ml, about 2.8 mg/ml, about 2.85 mg/ml, about 2.9 mg/ml, about 2.95 mg/ml, or about 3.0 mg/ml in the final liquid formulation. In some embodiments, the surfactant is polysorbate 80 and is present in about 0.5 mg/ml in the final liquid formulation. In some embodiments, the surfactant is polysorbate 80 and is present in about 1.0 mg/ml in the final liquid formulation. In some embodiments, the surfactant is polysorbate 80 and is present in about 2.0 mg/ml in the final liquid formulation.

In some embodiments, the surfactant is present in about 1% w/w to about 15% w/w of the solids in the liquid formulation. In other embodiments, the surfactant is present in about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% of the solids in the liquid formulation.

In some embodiments, the surfactant is present in about 1% w/w to about 5% w/w of the solids in the liquid formulation. In other embodiments, the surfactant is present in about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% of the solids in the liquid formulation.

Additional Excipients

In further embodiments, the amlodipine liquid formulation described herein comprises additional excipients including, but not limited to flavoring agents, coloring agents and thickeners. Additional excipients such as bulking agents, tonicity agents and chelating agents are within the scope of the embodiments.

In another embodiment, the amlodipine liquid formulation comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. Flavoring agents can be used singly or in combinations of two or more. In certain embodiments, the amlodipine liquid formulation comprises a flavoring agent.

In further embodiments, the amlodipine liquid formulation comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide and mixtures thereof.

Thickeners impart viscosity or weight to the resultant liquid forms from the amlodipine formulation described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose, certain silicates (magnesium aluminum silicate, aluminum silicate, etc. such as Veegum, Bentonite, and Kaolin) and certain gums (xanthan gum, locust bean gum, etc.). In certain embodiments, the amlodipine liquid formulation comprises a thickener.

In further embodiments, the amlodipine liquid formulation does not comprise glycerol which may cause headache, stomach upset, and diarrhea.

Additional excipients are contemplated in the amlodipine liquid formulation embodiments. These additional excipients are selected based on function and compatibility with the amlodipine liquid formulations described herein and may be found, for example in *Remington: The Science and Practice of Pharmacy*, Nineteenth Ed (Easton, Pa.: Mack Publishing Company, 1995); Hoover, John E., *Remington's Pharmaceutical Sciences*, (Easton, Pa.: Mack Publishing Co 1975); Liberman, H. A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

Particle Size

The term "D50", as used herein, refers to a particle size in micrometers corresponding to 50% of the volume of the sampled particles being larger than, and 50% of the volume of the sampled particles being smaller than, the recited D50 value. Similarly, the term "D90" refers to a particle size in micrometers corresponding to 90% of the volume of the sampled particles being smaller than, and 10% of the volume of the sampled particles being larger than, the recited D90 value. The term "D10" refers to a particle size in micrometers corresponding to 10% of the volume of the sampled particles being smaller than, and 90% of the volume of the sampled particles being larger than, the recited D10 value.

In some embodiments, the suspension disclosed herein comprises amlodipine benzoate particles having a D90 value between about 20 μm and about 60 μm. In some embodiments, the suspension disclosed herein comprises amlodipine benzoate particles having a D90 value between about 20 μm and about 40 μm. In some embodiments, the suspension disclosed herein comprises amlodipine benzoate particles having a D90 value between about 25 μm and about 35 μm. In some embodiments, the suspension disclosed herein comprises amlodipine benzoate particles having a D90 value of about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, about 50 μm, about 51 μm, about 52 μm, about 53 μm, about 54 μm, about 55 μm, about 56 μm, about 57 μm, about 58 μm, about 59 μm, or about 60 μm.

In some embodiments, the suspension disclosed herein comprises amlodipine benzoate particles having a D50 value between about 5 μm and about 40 μm. In some embodiments, the suspension disclosed herein comprises amlodipine benzoate particles having a D50 value between about 5 μm and about 20 μm. In some embodiments, the suspension disclosed herein comprises amlodipine benzoate particles having a D50 value between about 10 μm and about 20 μm. In some embodiments, the suspension disclosed herein comprises amlodipine benzoate particles having a D50 value of about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, or about 40 μm.

In some embodiments, the suspension disclosed herein comprises amlodipine benzoate particles having a D10 value between about 1 μm and about 10 μm. In some embodiments, the suspension disclosed herein comprises amlodipine benzoate particles having a D10 value between about 1 μm and about 5 μm. In some embodiments, the suspension disclosed herein comprises amlodipine benzoate particles having a D10 value between about 5 μm and about 10 μm. In some embodiments, the suspension disclosed herein comprises amlodipine benzoate particles having a D10 value of about 1 μm, about 2 μm, about 3 μm, about 4 μm, about 5 μm, about 6 μm, about 7 μm, about 8 μm, about 9 μm, or about 10 μm.

Stability

The amlodipine liquid formulations described herein are stable in various storage conditions including refrigerated, ambient and accelerated conditions. Stable as used herein refers to amlodipine liquid formulations having about 95% or greater of the initial amlodipine amount and/or about 5% w/w or less total impurities or related substances at the end of a given storage period. In some embodiment, the impurity is amlodipine USP impurity A (A.K.A EP impurity D):

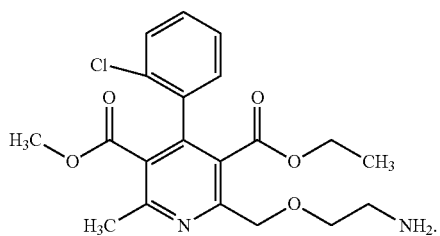 [SMILES: CCOC(=O)c1c(COCCN)nc(C)c(C(=O)OC)c1-c1ccccc1Cl]

The percentage of impurities is calculated from the amount of impurities relative to the amount of amlodipine. Stability is assessed by HPLC or any other known testing method. In some embodiments, the stable amlodipine liquid formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable amlodipine liquid formulations have about 5% w/w total impurities or related substances. In yet other embodiments, the stable amlodipine liquid formulations have about 4% w/w total impurities or related substances. In yet other embodiments, the stable amlodipine liquid formulations have about 3% w/w total impurities or related substances. In yet other embodiments, the stable amlodipine liquid formulations have about 2% w/w total impurities or related substances. In yet other embodiments, the stable amlodipine liquid formulations have about 1% w/w total impurities or related substances.

At refrigerated condition, the amlodipine liquid formulations described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, refrigerated condition is 5±5° C. In some embodiments, refrigerated condition is about 0° C., about 0.1° C., about 0.2° C., about 0.3° C., about 0.4° C., about 0.5° C., about 0.6° C., about 0.7° C., about 0.8° C., about 0.9° C., about 1° C., about 1.1° C., about 1.2° C., about 1.3° C., about 1.4° C., about 1.5° C., about 1.6° C., about 1.7° C., about 1.8° C., about 1.9° C., about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., about 8° C., about 8.1° C., about 8.2° C., about 8.3° C., about 8.4° C., about 8.5° C., about 8.6° C., about 8.7° C., about 8.8° C., about 8.9° C., about 9° C., about 9.1° C., about 9.2° C., about 9.3° C., about 9.4° C., about 9.5° C., about 9.6° C., about 9.7° C., about 9.8° C., about 9.9° C., or about 10° C. At accelerated conditions, the amlodipine liquid formulations described herein are stable for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months. Accelerated conditions for the amlodipine liquid formulations described herein include temperatures that are at or above ambient levels (25±5° C.). In some instances, an accelerated condition is at about 25° C., about 30° C., about 35° C., about 40° C., about 45° C., about 50° C., about 55° C., or about 60° C. Accelerated conditions for the amlodipine liquid formulations described herein also include relative humidity (RH) that are at or above ambient levels (55±10% RH). In other instances, an accelerated condition is above 55% RH, about 65% RH, about 70% RH, about 75% RH, or about 80% RH. In further instances, an accelerated condition is about 40° C. or 60° C. at ambient humidity. In yet further instances, an accelerated condition is about 40° C. at 75±5% RH humidity.

In some embodiments, the amlodipine liquid formulation is stable between about 5±5° C. and about 25±5° C. for at least 12 months. In one embodiment, the amlodipine liquid formulation is stable at about 5±5° C. for at least 12 months. In one embodiment, the amlodipine liquid formulation is stable at about 25±5° C. for at least 12 months. In one embodiment, the amlodipine liquid formulation is stable at about 5±5° C. for at least 24 months. In one embodiment, the amlodipine liquid formulation is stable at about 25±5° C. for at least 24 months.

Kits and Articles of Manufacture

For the amlodipine liquid formulations described herein, kits and articles of manufacture are also described. Such kits can comprise a carrier, package, or container that is compartmentalized to receive one or more containers such as vials, tubes, and the like, each of the container(s) comprising one of the separate elements to be used in a method described herein including an amlodipine liquid formulation. Suitable containers include, for example, bottles, vials, syringes, and test tubes. The containers can be formed from a variety of materials such as glass or plastic.

A kit will typically comprise one or more additional containers, each with one or more of various materials (such as reagents, optionally in concentrated form, and/or devices) desirable from a commercial and user standpoint for an amlodipine liquid formulation described herein. Non-limiting examples of such materials include, but not limited to, buffers, diluents, filters, needles, syringes; carrier, package, container, vial and/or tube labels listing contents and/or instructions for use, and package inserts with instructions for use associated with an amlodipine liquid formulation. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Method of Manufacturing

Disclosed herein is a process for preparing an amlodipine liquid formulation. In some embodiments, the amlodipine liquid formulation is in the form of a suspension. In some embodiments, the amlodipine liquid formulation comprises a pharmaceutically acceptable salt of amlodipine which is very slightly soluble in an aqueous media. In some embodiments, the amlodipine liquid formulation comprises a pharmaceutically acceptable salt of amlodipine which is practically insoluble in an aqueous media. In some embodiments, the amlodipine liquid formulation comprises amlodipine benzoate.

Described herein are processes for preparing amlodipine benzoate and suspensions comprising amlodipine benzoate. In some embodiment, ultrasonic agitation is used to generate the amlodipine benzoate.

Ultrasonic Agitation (Sonication)

In some embodiments, the ultrasonic agitation is carried out with any suitable sonication device such as those described in U.S. Pat. Nos. 5,471,001; 6,960,256; or an ultrasonic cleaning tank such as described in U.S. Pat. No. 3,516,645. Such devices are well known in the industry. The use of ultrasonic energy in conjunction with a solvent for cleaning workpieces is well established in the art. Cleaning apparatus of this type have been described, for instance, in U.S. Pat. Nos. 2,845,077; 3,293,456; 3,318,578; and 3,651,352.

By "sonication" it is meant that electrical energy is converted to physical vibrations (sound energy) which are applied to solutions, suspensions, or particles. In some embodiments, the sonication device has a sonication horn or probe that is inserted into the system of interest to emit sonic energy into the solution. In some embodiments, the sonicating device is operated at a frequency between about 1 kHz and about 10 MHz or between about 1 kHz and about 100 kHz or between about 20 kHz and about 40 kHz or any range or combination of ranges therein. In some embodiments, the frequency is modulated slightly around a target frequency. In some embodiments, the sonicating device is operated at a frequency of about 40 kHz with a modulation of about ±1 kHz. In some embodiments, other mixing devices such as homogenizers, blenders, or other stirring devices are used while subjecting the liquid to ultrasonic agitation.

Described herein is a process for preparing amlodipine benzoate, the process comprising:
  (i) providing an aqueous mixture comprising an amlodipine salt that is more soluble in aqueous media than amlodipine benzoate;
  (ii) adding a salt forming agent to the aqueous mixture to form a first mixture;
  (iii) subjecting the first mixture to ultrasonic agitation thereby forming a second mixture comprising amlodipine benzoate.

In some embodiments of a method of preparing amlodipine benzoate, the process further comprises adjusting the pH of the aqueous mixture comprising an amlodipine salt that is more soluble in aqueous media than amlodipine benzoate (e.g., amlodipine besylate).

In some embodiments of a method of preparing amlodipine benzoate, the aqueous mixture further comprises a surfactant (e.g. polysorbate 80).

In some embodiments of a method of preparing amlodipine benzoate, the surfactant (e.g., polysorbate 80) is added to the aqueous mixture of step (i) and mixed prior to the addition of the amlodipine salt that is more soluble in aqueous media than amlodipine benzoate (e.g., amlodipine besylate). This surfactant addition prior to the addition of the amlodipine salt that is more soluble in aqueous media that amlodipine benzoate (e.g., amlodipine besylate) minimizes the potential for amlodipine to adhere to metal containers such as those made of stainless steel.

In some embodiments of a method of preparing amlodipine benzoate, the aqueous mixture comprising the amlodipine salt that is more soluble in aqueous media than amlodipine benzoate (e.g., amlodipine besylate) and the surfactant (e.g., polysorbate 80) is mixed prior to the addition of the salt forming agent (e.g., sodium benzoate or benzoic acid) in step (ii). This mixing ensures an even dispersion of the amlodipine salt and the surfactant (e.g., polysorbate 80). In some embodiments of a method of preparing amlodipine benzoate, the mixing prior to the addition of the salt forming agent (e.g., sodium benzoate or benzoic acid) in step (ii) is performed for between about 1 minute and about 10 minutes. In some embodiments of a method of preparing amlodipine benzoate, the mixing prior to the addition of the salt forming agent (e.g., sodium benzoate or benzoic acid) in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed before being subjected to ultrasonic agitation.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed while being subjected to ultrasonic agitation.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed after being subjected to ultrasonic agitation.

In some embodiments of a method of preparing amlodipine benzoate, the mixing after being subjected to ultrasonic agitation is performed for between about 1 minute and about 30 minutes. In some embodiments of a method of preparing amlodipine benzoate, the mixing after being subjected to ultrasonic agitation is performed for between about 10 minutes and about 30 minutes. In some embodiments of a method of preparing amlodipine benzoate, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing amlodipine benzoate, the frequency of the ultrasonic agitation is between about 20 kHz and about 100 kHz. In some embodiments of a method of preparing amlodipine benzoate, the frequency of the ultrasonic agitation is about 20 kHz. In some embodiments of a method of preparing amlodipine benzoate, the frequency of the ultrasonic agitation is about 40 kHz. In some embodiments of a method of preparing amlodipine benzoate, the frequency of the ultrasonic agitation is modulated about ±1 kHz around the desired frequency.

In some embodiments of a method of preparing amlodipine benzoate, the duration of the ultrasonic agitation is between about 1 minute and 1 hour. In some embodiments of a method of preparing amlodipine benzoate, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing amlodipine benzoate, the duration of the ultrasonic agitation is between about 5 minutes and 30 minutes. In some embodiments of a method of preparing amlodipine benzoate, the duration of the ultrasonic agitation is between about 5 minutes and 20 minutes. In some embodiments of a method of preparing amlodipine benzoate, the duration of the ultrasonic agitation is about 5 minutes. In some embodiments of a method of preparing amlodipine benzoate, the duration of the ultrasonic agitation is about 10 minutes.

In some embodiments of a method of preparing amlodipine benzoate, the temperature of the first mixture or second mixture is not controlled.

In some embodiments of a method of preparing amlodipine benzoate, the process does not involve the use of any solvent other than water.

Described herein is a process for preparing amlodipine benzoate, the process comprising:
(i) providing an aqueous mixture comprising an amlodipine salt that is more soluble in aqueous media than amlodipine benzoate;
(ii) adding sodium benzoate to the aqueous mixture to form a first mixture;
(iii) subjecting the first mixture to ultrasonic agitation thereby forming a second mixture comprising amlodipine benzoate.

In some embodiments of a method of preparing amlodipine benzoate, the aqueous mixture further comprises a surfactant (e.g., polysorbate 80).

In some embodiments of a method of preparing amlodipine benzoate, the surfactant (e.g., polysorbate 80) is added to the aqueous mixture of step (i) and mixed prior to the addition of the amlodipine salt that is more soluble in aqueous media than amlodipine benzoate (e.g., amlodipine besylate). This surfactant addition prior to the addition of the amlodipine salt that is more soluble in aqueous media that amlodipine benzoate (e.g., amlodipine besylate) minimizes the potential for amlodipine to adhere to metal containers such as those made of stainless steel.

In some embodiments of a method of preparing amlodipine benzoate, the aqueous mixture comprising the amlodipine salt that is more soluble in aqueous media than amlodipine benzoate (e.g., amlodipine besylate) and the surfactant (e.g., polysorbate 80) is mixed prior to the addition of sodium benzoate in step (ii). This mixing ensures an even dispersion of the amlodipine salt and the surfactant (e.g., polysorbate 80). In some embodiments of a method of preparing amlodipine benzoate, the mixing prior to the addition of sodium benzoate in step (ii) is performed for between about 1 minute and about 10 minutes. In some embodiments of a method of preparing amlodipine benzoate, the mixing prior to the addition of sodium benzoate in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and sodium benzoate is mixed before being subjected to ultrasonic agitation.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and sodium benzoate is mixed while being subjected to ultrasonic agitation.

In some embodiments of a method of preparing amlodipine benzoate, the first mixture comprising the amlodipine salt that is more soluble in aqueous media than amlodipine benzoate (e.g., amlodipine besylate), the surfactant (e.g., polysorbate 80), and sodium benzoate is mixed after being subjected to ultrasonic agitation.

In some embodiments of a method of preparing amlodipine benzoate, the mixing after being subjected to ultrasonic agitation is performed for between about 1 minute and about 30 minutes. In some embodiments of a method of preparing amlodipine benzoate, the mixing after being subjected to ultrasonic agitation is performed for between about 10 minutes and about 30 minutes. In some embodiments of a method of preparing amlodipine benzoate, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing amlodipine benzoate, the frequency of the ultrasonic agitation is between about 20 kHz and about 100 kHz. In some embodiments of a method of preparing amlodipine benzoate, the frequency of the ultrasonic agitation is about 20 kHz. In some embodiments of a method of preparing amlodipine benzoate, the frequency of the ultrasonic agitation is about 40 kHz. In some embodiments of a method of preparing amlodipine benzoate, the frequency of the ultrasonic agitation is modulated about ±1 kHz around the desired frequency.

In some embodiments of a method of preparing amlodipine benzoate, the duration of the ultrasonic agitation is between about 1 minute and 1 hour. In some embodiments of a method of preparing amlodipine benzoate, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing amlodipine benzoate, the duration of the ultrasonic agitation is between about 5 minutes and 30 minutes. In some embodiments of a method of preparing amlodipine benzoate, the duration of the ultrasonic agitation is between about 5 minutes and 20 minutes. In some embodiments of a method of preparing amlodipine benzoate, the duration of the ultrasonic agitation is about 5 minutes. In some embodiments of a method of preparing amlodipine benzoate, the duration of the ultrasonic agitation is about 10 minutes.

In some embodiments of a method of preparing amlodipine benzoate, the temperature of the first mixture or second mixture is not controlled.

In some embodiments of a method of preparing amlodipine benzoate, the process does not involve the use of any solvent other than water.

Described herein is a process for preparing amlodipine naphthalene sulfonate, the process comprising:
(i) providing an aqueous mixture comprising an amlodipine salt that is more soluble in aqueous media than amlodipine naphthalene sulfonate;
(ii) adding a salt forming agent to the aqueous mixture to form a first mixture;
(iii) subjecting the first mixture to ultrasonic agitation thereby forming a second mixture comprising amlodipine naphthalene sulfonate.

In some embodiments of a method of preparing amlodipine naphthalene sulfonate, the process further comprises adjusting the pH of the aqueous mixture comprising an amlodipine salt that is more soluble in aqueous media than amlodipine naphthalene sulfonate (e.g., amlodipine besylate).

In some embodiments of a method of preparing amlodipine naphthalene sulfonate, the aqueous mixture further comprises a surfactant (e.g. polysorbate 80).

In some embodiments of a method of preparing amlodipine naphthalene sulfonate, the surfactant (e.g., polysorbate 80) is added to the aqueous mixture of step (i) and mixed prior to the addition of the amlodipine salt that is more soluble in aqueous media than amlodipine naphthalene sulfonate (e.g., amlodipine besylate). This surfactant addition prior to the addition of the amlodipine salt that is more soluble in aqueous media that amlodipine naphthalene sulfonate (e.g., amlodipine besylate) minimizes the potential for amlodipine to adhere to metal containers such as those made of stainless steel.

In some embodiments of a method of preparing amlodipine naphthalene sulfonate, the aqueous mixture comprising the amlodipine salt that is more soluble in aqueous media than amlodipine naphthalene sulfonate (e.g., amlodipine besylate) and the surfactant (e.g., polysorbate 80) is mixed prior to the addition of the salt forming agent (e.g., sodium naphthalene-2-sulfonate) in step (ii). This mixing ensures an even dispersion of the amlodipine salt and the surfactant (e.g., polysorbate 80). In some embodiments of a method of preparing amlodipine naphthalene sulfonate, the mixing prior to the addition of the salt forming agent (e.g., sodium naphthalene-2-sulfonate) in step (ii) is performed for between about 1 minute and about 10 minutes. In some embodiments of a method of preparing amlodipine naphthalene sulfonate, the mixing prior to the addition of the salt forming agent (e.g., sodium naphthalene-2-sulfonate) in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed before being subjected to ultrasonic agitation.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed while being subjected to ultrasonic agitation.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed after being subjected to ultrasonic agitation.

In some embodiments of a method of preparing amlodipine naphthalene sulfonate, the mixing after being subjected to ultrasonic agitation is performed for between about 1 minute and about 30 minutes. In some embodiments of a method of preparing amlodipine naphthalene sulfonate, the mixing after being subjected to ultrasonic agitation is performed for between about 10 minutes and about 30 minutes. In some embodiments of a method of preparing amlodipine naphthalene sulfonate, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing amlodipine naphthalene sulfonate, the frequency of the ultrasonic agitation is between about 20 kHz and about 100 kHz. In some embodiments of a method of preparing amlodipine naphthalene sulfonate, the frequency of the ultrasonic agitation is about 20 kHz. In some embodiments of a method of preparing amlodipine naphthalene sulfonate, the frequency of the ultrasonic agitation is about 40 kHz. In some embodiments of a method of preparing amlodipine naphthalene sulfonate, the frequency of the ultrasonic agitation is modulated about ±1 kHz around the desired frequency.

In some embodiments of a method of preparing amlodipine naphthalene sulfonate, the duration of the ultrasonic agitation is between about 1 minute and 1 hour. In some embodiments of a method of preparing amlodipine naphthalene sulfonate, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing amlodipine naphthalene sulfonate, the duration of the ultrasonic agitation is between about 5 minutes and 30 minutes. In some embodiments of a method of preparing amlodipine naphthalene sulfonate, the duration of the ultrasonic agitation is between about 5 minutes and 20 minutes. In some embodiments of a method of preparing amlodipine naphthalene sulfonate, the duration of the ultrasonic agitation is about 5 minutes. In some embodiments of a method of preparing amlodipine naphthalene sulfonate, the duration of the ultrasonic agitation is about 10 minutes.

In some embodiments of a method of preparing amlodipine naphthalene sulfonate, the temperature of the first mixture or second mixture is not controlled.

In some embodiments of a method of preparing amlodipine naphthalene sulfonate, the process does not involve the use of any solvent other than water.

Described herein is a process for preparing amlodipine naphthalene sulfonate, the process comprising:
(i) providing an aqueous mixture comprising an amlodipine salt that is more soluble in aqueous media than amlodipine naphthalene sulfonate;
(ii) adding sodium naphthalene-2-sulfonate to the aqueous mixture to form a first mixture;
(iii) subjecting the first mixture to ultrasonic agitation thereby forming a second mixture comprising amlodipine naphthalene sulfonate.

In some embodiments of a method of preparing amlodipine naphthalene sulfonate, the aqueous mixture further comprises a surfactant (e.g., polysorbate 80).

In some embodiments of a method of preparing amlodipine naphthalene sulfonate, the surfactant (e.g., polysorbate 80) is added to the aqueous mixture of step (i) and mixed prior to the addition of the amlodipine salt that is more soluble in aqueous media than amlodipine naphthalene sulfonate (e.g., amlodipine besylate). This surfactant addition prior to the addition of the amlodipine salt that is more soluble in aqueous media that amlodipine naphthalene sulfonate (e.g., amlodipine besylate) minimizes the potential for amlodipine to adhere to metal containers such as those made of stainless steel.

In some embodiments of a method of preparing amlodipine naphthalene sulfonate, the aqueous mixture comprising the amlodipine salt that is more soluble in aqueous media than amlodipine naphthalene sulfonate (e.g., amlodipine besylate) and the surfactant (e.g., polysorbate 80) is mixed prior to the addition of sodium naphthalene-2-sulfonate in step (ii). This mixing ensures an even dispersion of the amlodipine salt and the surfactant (e.g., polysorbate 80). In some embodiments of a method of preparing amlodipine naphthalene sulfonate, the mixing prior to the addition of sodium naphthalene-2-sulfonate in step (ii) is performed for between about 1 minute and about 10 minutes. In some embodiments of a method of preparing amlodipine naphthalene sulfonate, the mixing prior to the addition of sodium naphthalene-2-sulfonate in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed before being subjected to ultrasonic agitation.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed while being subjected to ultrasonic agitation.

In some embodiments of a method of preparing amlodipine naphthalene sulfonate, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed after being subjected to ultrasonic agitation.

In some embodiments of a method of preparing amlodipine naphthalene sulfonate, the mixing after being subjected to ultrasonic agitation is performed for between about 1 minute and about 30 minutes. In some embodiments of a method of preparing amlodipine naphthalene sulfonate, the mixing after being subjected to ultrasonic agitation is performed for between about 10 minutes and about 30 minutes. In some embodiments of a method of preparing amlodipine naphthalene sulfonate, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing amlodipine naphthalene sulfonate, the frequency of the ultrasonic agitation is between about 20 kHz and about 100 kHz. In some embodiments of a method of preparing amlodipine naphthalene sulfonate, the frequency of the ultrasonic agitation is about 20 kHz. In some embodiments of a method of preparing amlodipine naphthalene sulfonate, the frequency of the ultrasonic agitation is about 40 kHz. In some embodiments of a method of preparing amlodipine naphthalene sulfonate, the frequency of the ultrasonic agitation is modulated about ±1 kHz around the desired frequency.

In some embodiments of a method of preparing amlodipine naphthalene sulfonate, the duration of the ultrasonic agitation is between about 1 minute and 1 hour. In some embodiments of a method of preparing amlodipine naphthalene sulfonate, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing amlodipine naphthalene sulfonate, the duration of the ultrasonic agitation is between about 5 minutes and 30 minutes. In some embodiments of a method of preparing amlodipine naphthalene sulfonate, the duration of the ultrasonic agitation is between about 5 minutes and 20 minutes. In some embodiments of a method of preparing amlodipine naphthalene sulfonate, the duration of the ultrasonic agitation is about 5 minutes. In some embodiments of a method of preparing amlodipine naphthalene sulfonate, the duration of the ultrasonic agitation is about 10 minutes.

In some embodiments of a method of preparing amlodipine naphthalene sulfonate, the temperature of the first mixture or second mixture is not controlled.

In some embodiments of a method of preparing amlodipine naphthalene sulfonate, the process does not involve the use of any solvent other than water.

Described herein is a process for preparing an amlodipine benzoate suspension, the process comprising:
(i) providing an aqueous mixture comprising an amlodipine salt that is more soluble in aqueous media than amlodipine benzoate;
(ii) adding a salt forming agent to the aqueous mixture to form a first mixture;
(iii) subjecting the first mixture to ultrasonic agitation thereby forming a second mixture comprising amlodipine benzoate.

In some embodiments of a method of preparing an amlodipine benzoate suspension, the process further comprises adjusting the pH of the aqueous mixture comprising an amlodipine salt that is more soluble in aqueous media than amlodipine benzoate (e.g., amlodipine besylate).

In some embodiments of a method of preparing an amlodipine benzoate suspension, the aqueous mixture further comprises a surfactant (e.g. polysorbate 80).

In some embodiments of a method of preparing amlodipine benzoate, the surfactant (e.g., polysorbate 80) is added to the aqueous mixture of step (i) and mixed prior to the addition of the amlodipine salt that is more soluble in aqueous media than amlodipine benzoate (e.g., amlodipine besylate). This surfactant addition prior to the addition of the amlodipine salt that is more soluble in aqueous media that amlodipine benzoate (e.g., amlodipine besylate) minimizes the potential for amlodipine to adhere to metal containers such as those made of stainless steel.

In some embodiments of a method of preparing an amlodipine benzoate suspension, the aqueous mixture comprising the amlodipine salt that is more soluble in aqueous media than amlodipine benzoate (e.g., amlodipine besylate) and the surfactant (e.g., polysorbate 80) is mixed prior to the addition of the salt forming agent (e.g., sodium benzoate or benzoic acid) in step (ii). This mixing ensures an even dispersion of the amlodipine salt and the surfactant (e.g., polysorbate 80). In some embodiments of a method of preparing an amlodipine benzoate suspension, the mixing prior to the addition of the salt forming agent (e.g., sodium benzoate or benzoic acid) in step (ii) is performed for between about 1 minute and about 10 minutes. In some embodiments of a method of preparing an amlodipine benzoate suspension, the mixing prior to the addition of the salt forming agent (e.g., sodium benzoate or benzoic acid) in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed before being subjected to ultrasonic agitation.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed while being subjected to ultrasonic agitation.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and the salt forming agent (e.g., sodium benzoate or benzoic acid) is mixed after being subjected to ultrasonic agitation.

In some embodiments of a method of preparing an amlodipine benzoate suspension, the mixing after being subjected to ultrasonic agitation is performed for between about 1 minute and about 30 minutes. In some embodiments of a method of preparing an amlodipine benzoate suspension, the mixing after being subjected to ultrasonic agitation is performed for between about 10 minutes and about 30 minutes. In some embodiments of a method of preparing an amlodipine benzoate suspension, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing an amlodipine benzoate suspension, the frequency of the ultrasonic agitation is between about 20 kHz and about 100 kHz. In some embodiments of a method of preparing an amlodipine benzoate suspension, the frequency of the ultrasonic agitation is about 20 kHz. In some embodiments of a method of preparing an amlodipine benzoate suspension, the frequency of the ultrasonic agitation is about 40 kHz. In some embodiments of a method of preparing amlodipine benzoate, the frequency of the ultrasonic agitation is modulated about ±1 kHz around the desired frequency.

In some embodiments of a method of preparing an amlodipine benzoate suspension, the duration of the ultrasonic agitation is between about 1 minute and 1 hour. In some embodiments of a method of preparing an amlodipine benzoate suspension, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing an amlodipine benzoate suspension, the duration of the ultrasonic agitation is between about 5 minutes and 30 minutes. In some embodiments of a method of preparing an amlodipine benzoate suspension, the duration of the ultrasonic agitation is between about 5 minutes and 20 minutes. In some embodiments of a method of preparing an amlodipine benzoate suspension, the duration of the ultrasonic agitation is about 5 minutes. In some embodiments of a method of preparing an amlodipine benzoate suspension, the duration of the ultrasonic agitation is about 10 minutes.

In some embodiments of a method of preparing an amlodipine benzoate suspension, the temperature of the first mixture or second mixture is not controlled.

In some embodiments of a method of preparing an amlodipine benzoate suspension, the process does not involve the use of any solvent other than water.

In some embodiments of a method of preparing an amlodipine benzoate suspension, the process further comprises adding the second mixture comprising amlodipine benzoate to a third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine benzoate suspension, the process further comprises adding a second surfactant (e.g., polysorbate 80).

In some embodiments of a method of preparing an amlodipine benzoate suspension, the second surfactant (e.g., polysorbate 80) is added to the second mixture and/or the third mixture.

In some embodiments of a method of preparing an amlodipine benzoate suspension, the second surfactant is added to the second mixture comprising amlodipine benzoate.

In some embodiments of a method of preparing an amlodipine benzoate suspension, a second surfactant is added to the third mixture comprising one or more of a buffer, a preservative, a sweetening agent, a suspension agent, an antifoaming agent, and a flavoring agent.

In some embodiments of a method of preparing an amlodipine benzoate suspension, the process further comprises adding water quantum satis thereby forming the amlodipine benzoate suspension.

Also disclosed herein is a process for preparing an amlodipine benzoate suspension, the process comprising:
(i) providing an aqueous mixture comprising an amlodipine salt that is more soluble in aqueous media than amlodipine benzoate;
(ii) adding sodium benzoate to the aqueous mixture to form a first mixture;
(iii) subjecting the first mixture to ultrasonic agitation thereby forming a second mixture comprising amlodipine benzoate.

In some embodiments of a method of preparing an amlodipine benzoate suspension, the aqueous mixture further comprises a surfactant (e.g., polysorbate 80).

In some embodiments of a method of preparing amlodipine benzoate, the surfactant (e.g., polysorbate 80) is added to the aqueous mixture of step (i) and mixed prior to the addition of the amlodipine salt that is more soluble in aqueous media than amlodipine benzoate (e.g., amlodipine besylate). This surfactant addition prior to the addition of the amlodipine salt that is more soluble in aqueous media that amlodipine benzoate (e.g., amlodipine besylate) minimizes the potential for amlodipine to adhere to metal containers such as those made of stainless steel.

In some embodiments of a method of preparing an amlodipine benzoate suspension, the aqueous mixture comprising the amlodipine salt that is more soluble in aqueous media than amlodipine benzoate (e.g., amlodipine besylate) and the surfactant (e.g., polysorbate 80) is mixed prior to the addition of sodium benzoate in step (ii). This mixing ensures an even dispersion of the amlodipine salt and the surfactant (e.g., polysorbate 80). In some embodiments of a method of preparing an amlodipine benzoate suspension, the mixing prior to the addition of sodium benzoate in step (ii) is performed for between about 1 minute and about 10 minutes. In some embodiments of a method of preparing an amlodipine benzoate suspension, the mixing prior to the addition of sodium benzoate in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and sodium benzoate is mixed before being subjected to ultrasonic agitation.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and sodium benzoate is mixed while being subjected to ultrasonic agitation.

In some embodiments of a method of preparing an amlodipine benzoate suspension, the first mixture comprising the amlodipine salt that is more soluble in aqueous media than amlodipine benzoate (e.g., amlodipine besylate), the surfactant (e.g., polysorbate 80), and sodium benzoate is mixed after being subjected to ultrasonic agitation.

In some embodiments of a method of preparing an amlodipine benzoate suspension, the mixing after being subjected to ultrasonic agitation is performed for between about 1 minute and about 30 minutes. In some embodiments of a method of preparing an amlodipine benzoate suspension, the mixing after being subjected to ultrasonic agitation is performed for between about 10 minutes and about 30 minutes. In some embodiments of a method of preparing an amlodipine benzoate suspension, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing an amlodipine benzoate suspension, the frequency of the ultrasonic agitation is between about 20 kHz and about 100 kHz. In some embodiments of a method of preparing an amlodipine benzoate suspension, the frequency of the ultrasonic agitation is about 20 kHz. In some embodiments of a method of preparing an amlodipine benzoate suspension, the frequency of the ultrasonic agitation is about 40 kHz. In some embodiments of a method of preparing amlodipine benzoate, the frequency of the ultrasonic agitation is modulated about ±1 kHz around the desired frequency.

In some embodiments of a method of preparing an amlodipine benzoate suspension, the duration of the ultrasonic agitation is between about 1 minute and 1 hour. In some embodiments of a method of preparing an amlodipine benzoate suspension, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing an amlodipine benzoate suspension, the duration of the ultrasonic agitation is between about 5 minutes and 30 minutes. In some embodiments of a method of preparing an amlodipine benzoate suspension, the duration of the ultrasonic agitation is between about 5 minutes and 20 minutes. In some embodiments of a method of preparing an amlodipine benzoate suspension, the duration of the ultrasonic agitation is about 5 minutes. In some embodiments of a method of preparing an amlodipine benzoate suspension, the duration of the ultrasonic agitation is about 10 minutes.

In some embodiments of a method of preparing an amlodipine benzoate suspension, the temperature of the first mixture or the second mixture is not controlled.

In some embodiments of a method of preparing an amlodipine benzoate suspension, the process does not involve the use of any solvent other than water.

In some embodiments of a method of preparing an amlodipine benzoate suspension, the process further comprises adding the second mixture comprising amlodipine benzoate to a third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine benzoate suspension, the process further comprises adding a second surfactant (e.g., polysorbate 80).

In some embodiments of a method of preparing an amlodipine benzoate suspension, the second surfactant (e.g., polysorbate 80) is added to the second mixture and/or the third mixture.

In some embodiments of a method of preparing an amlodipine benzoate suspension, the second surfactant is added to the second mixture comprising amlodipine benzoate.

In some embodiments of a method of preparing an amlodipine benzoate suspension, a second surfactant is added to the third mixture comprising one or more of a buffer, a preservative, a sweetening agent, a suspension agent, an antifoaming agent, water, and a flavoring agent.

In some embodiments of a method of preparing an amlodipine benzoate suspension, the process further comprises adding water quantum satis thereby forming the amlodipine benzoate suspension.

Described herein is a process for preparing an amlodipine naphthalene sulfonate suspension, the process comprising:
(i) providing an aqueous mixture comprising an amlodipine salt that is more soluble in aqueous media than amlodipine naphthalene sulfonate;
(ii) adding a salt forming agent to the aqueous mixture to form a first mixture;
(iii) subjecting the first mixture to ultrasonic agitation thereby forming a second mixture comprising amlodipine naphthalene sulfonate.

In some embodiments of a method of preparing an amlodipine naphthalene sulfonate suspension, the process further comprises adjusting the pH of the aqueous mixture comprising an amlodipine salt that is more soluble in aqueous media than amlodipine naphthalene sulfonate (e.g., amlodipine besylate).

In some embodiments of a method of preparing an amlodipine naphthalene sulfonate suspension, the aqueous mixture further comprises a surfactant (e.g. polysorbate 80).

In some embodiments of a method of preparing amlodipine naphthalene sulfonate, the surfactant (e.g., polysorbate 80) is added to the aqueous mixture of step (i) and mixed prior to the addition of the amlodipine salt that is more soluble in aqueous media than amlodipine naphthalene sulfonate (e.g., amlodipine besylate). This surfactant addition prior to the addition of the amlodipine salt that is more soluble in aqueous media that amlodipine naphthalene sulfonate (e.g., amlodipine besylate) minimizes the potential for amlodipine to adhere to metal containers such as those made of stainless steel.

In some embodiments of a method of preparing an amlodipine naphthalene sulfonate suspension, the aqueous mixture comprising the amlodipine salt that is more soluble in aqueous media than amlodipine naphthalene sulfonate (e.g., amlodipine besylate) and the surfactant (e.g., polysorbate 80) is mixed prior to the addition of the salt forming agent (e.g., sodium naphthalene-2-sulfonate) in step (ii). This mixing ensures an even dispersion of the amlodipine salt and the surfactant (e.g., polysorbate 80). In some embodiments of a method of preparing an amlodipine naphthalene sulfonate suspension, the mixing prior to the addition of the salt forming agent (e.g., sodium naphthalene-2-sulfonate) in step (ii) is performed for between about 1 minute and about 10 minutes. In some embodiments of a method of preparing an amlodipine naphthalene sulfonate suspension, the mixing prior to the addition of the salt forming agent (e.g., sodium naphthalene-2-sulfonate) in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed before being subjected to ultrasonic agitation.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed while being subjected to ultrasonic agitation.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and the salt forming agent (e.g., sodium naphthalene-2-sulfonate) is mixed after being subjected to ultrasonic agitation.

In some embodiments of a method of preparing an amlodipine naphthalene sulfonate suspension, the mixing after being subjected to ultrasonic agitation is performed for between about 1 minute and about 30 minutes. In some embodiments of a method of preparing an amlodipine naphthalene sulfonate suspension, the mixing after being subjected to ultrasonic agitation is performed for between about 10 minutes and about 30 minutes. In some embodiments of a method of preparing an amlodipine naphthalene sulfonate suspension, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing an amlodipine naphthalene sulfonate suspension, the frequency of the ultrasonic agitation is between about 20 kHz and about 100 kHz. In some embodiments of a method of preparing an amlodipine naphthalene sulfonate suspension, the frequency of the ultrasonic agitation is about 20 kHz. In some embodiments of a method of preparing an amlodipine naphthalene sulfonate suspension, the frequency of the ultrasonic agitation is about 40 kHz. In some embodiments of a method of preparing amlodipine naphthalene sulfonate, the frequency of the ultrasonic agitation is modulated about ±1 kHz around the desired frequency.

In some embodiments of a method of preparing an amlodipine naphthalene sulfonate suspension, the duration of the ultrasonic agitation is between about 1 minute and 1 hour. In some embodiments of a method of preparing an amlodipine naphthalene sulfonate suspension, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing an amlodipine naphthalene sulfonate suspension, the duration of the ultrasonic agitation is between about 5 minutes and 30 minutes. In some embodiments of a method of preparing an amlodipine naphthalene sulfonate suspension, the duration of the ultrasonic agitation is between about 5 minutes and 20 minutes. In some embodiments of a method of preparing an amlodipine naphthalene sulfonate suspension, the duration of the ultrasonic agitation is about 5 minutes. In some embodiments of a method of preparing an amlodipine naphthalene sulfonate suspension, the duration of the ultrasonic agitation is about 10 minutes.

In some embodiments of a method of preparing an amlodipine naphthalene sulfonate suspension, the temperature of the first mixture or second mixture is not controlled.

In some embodiments of a method of preparing an amlodipine naphthalene sulfonate suspension, the process does not involve the use of any solvent other than water.

In some embodiments of a method of preparing an amlodipine naphthalene sulfonate suspension, the process further comprises adding the second mixture comprising amlodipine naphthalene sulfonate to a third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine naphthalene sulfonate suspension, the process further comprises adding a second surfactant (e.g., polysorbate 80).

In some embodiments of a method of preparing an amlodipine naphthalene sulfonate suspension, the second surfactant (e.g., polysorbate 80) is added to the second mixture and/or the third mixture.

In some embodiments of a method of preparing an amlodipine naphthalene sulfonate suspension, the second surfactant is added to the second mixture comprising amlodipine naphthalene sulfonate.

In some embodiments of a method of preparing an amlodipine naphthalene sulfonate suspension, a second surfactant is added to the third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine naphthalene sulfonate suspension, the process further comprises adding water quantum satis thereby forming the amlodipine naphthalene sulfonate suspension.

Also disclosed herein is a process for preparing an amlodipine naphthalene sulfonate suspension, the process comprising:
(i) providing an aqueous mixture comprising an amlodipine salt that is more soluble in aqueous media than amlodipine naphthalene sulfonate;
(ii) adding sodium naphthalene-2-sulfonate to the aqueous mixture to form a first mixture;
(iii) subjecting the first mixture to ultrasonic agitation thereby forming a second mixture comprising amlodipine naphthalene sulfonate.

In some embodiments of a method of preparing an amlodipine naphthalene sulfonate suspension, the aqueous mixture further comprises a surfactant (e.g., polysorbate 80).

In some embodiments of a method of preparing amlodipine naphthalene sulfonate, the surfactant (e.g., polysorbate 80) is added to the aqueous mixture of step (i) and mixed prior to the addition of the amlodipine salt that is more soluble in aqueous media than amlodipine naphthalene sulfonate (e.g., amlodipine besylate). This surfactant addition prior to the addition of the amlodipine salt that is more soluble in aqueous media that amlodipine naphthalene sulfonate (e.g., amlodipine besylate) minimizes the potential for amlodipine to adhere to metal containers such as those made of stainless steel.

In some embodiments of a method of preparing an amlodipine naphthalene sulfonate suspension, the aqueous mixture comprising the amlodipine salt that is more soluble in aqueous media than amlodipine naphthalene sulfonate (e.g., amlodipine besylate) and the surfactant (e.g., polysorbate 80) is mixed prior to the addition of sodium naphthalene-2-sulfonate in step (ii). This mixing ensures an even dispersion of the amlodipine salt and the surfactant (e.g., polysorbate 80). In some embodiments of a method of preparing an amlodipine naphthalene sulfonate suspension, the mixing prior to the addition of sodium naphthalene-2-sulfonate in step (ii) is performed for between about 1 minute and about 10 minutes. In some embodiments of a method of preparing an amlodipine naphthalene sulfonate suspension, the mixing prior to the addition of sodium naphthalene-2-sulfonate in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed before being subjected to ultrasonic agitation.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed while being subjected to ultrasonic agitation.

In some embodiments of a method of preparing an amlodipine naphthalene sulfonate suspension, the first mixture comprising the amlodipine salt that is more soluble in aqueous media than amlodipine naphthalene sulfonate (e.g., amlodipine besylate), the surfactant (e.g., polysorbate 80), and sodium naphthalene-2-sulfonate is mixed after being subjected to ultrasonic agitation.

In some embodiments of a method of preparing an amlodipine naphthalene sulfonate suspension, the mixing after being subjected to ultrasonic agitation is performed for between about 1 minute and about 30 minutes. In some embodiments of a method of preparing an amlodipine naphthalene sulfonate suspension, the mixing after being subjected to ultrasonic agitation is performed for between about 10 minutes and about 30 minutes. In some embodiments of a method of preparing an amlodipine naphthalene sulfonate suspension, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing an amlodipine naphthalene sulfonate suspension, the frequency of the ultrasonic agitation is between about 20 kHz and about 100 kHz. In some embodiments of a method of preparing an amlodipine naphthalene sulfonate suspension, the frequency of the ultrasonic agitation is about 20 kHz. In some embodiments of a method of preparing an amlodipine naphthalene sulfonate suspension, the frequency of the ultrasonic agitation is about 40 kHz. In some embodiments of a method of preparing amlodipine naphthalene sulfonate, the frequency of the ultrasonic agitation is modulated about ±1 kHz around the desired frequency.

In some embodiments of a method of preparing an amlodipine naphthalene sulfonate suspension, the duration of the ultrasonic agitation is between about 1 minute and 1 hour. In some embodiments of a method of preparing an amlodipine naphthalene sulfonate suspension, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing an amlodipine naphthalene sulfonate suspension, the duration of the ultrasonic agitation is between about 5 minutes and 30 minutes. In some embodiments of a method of preparing an amlodipine naphthalene sulfonate suspension, the duration of the ultrasonic agitation is between about 5 minutes and 20 minutes. In some embodiments of a method of preparing an amlodipine naphthalene sulfonate suspension, the duration of the ultrasonic agitation is about 5 minutes. In some embodiments of a method of preparing an amlodipine naphthalene sulfonate suspension, the duration of the ultrasonic agitation is about 10 minutes.

In some embodiments of a method of preparing an amlodipine naphthalene sulfonate suspension, the temperature of the first mixture or the second mixture is not controlled.

In some embodiments of a method of preparing an amlodipine naphthalene sulfonate suspension, the process does not involve the use of any solvent other than water.

In some embodiments of a method of preparing an amlodipine naphthalene sulfonate suspension, the process further comprises adding the second mixture comprising amlodipine naphthalene sulfonate to a third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine naphthalene sulfonate suspension, the process further comprises adding a second surfactant (e.g., polysorbate 80).

In some embodiments of a method of preparing an amlodipine naphthalene sulfonate suspension, the second surfactant (e.g., polysorbate 80) is added to the second mixture and/or the third mixture.

In some embodiments of a method of preparing an amlodipine naphthalene sulfonate suspension, the second surfactant is added to the second mixture comprising amlodipine naphthalene sulfonate.

In some embodiments of a method of preparing an amlodipine naphthalene sulfonate suspension, a second surfactant is added to the third mixture comprising one or more of a buffer, a preservative, a sweetening agent, a suspension agent, an antifoaming agent, and a flavoring agent.

In some embodiments of a method of preparing an amlodipine naphthalene sulfonate suspension, the process further comprises adding water quantum satis thereby forming the amlodipine naphthalene sulfonate suspension.

Also disclosed herein is a process for preparing an amlodipine benzoate suspension, the process comprising:
  (i) providing an amlodipine besylate aqueous mixture;
  (ii) adding sodium benzoate to the aqueous mixture to form a first mixture;
  (iii) subjecting the first mixture to ultrasonic agitation thereby forming a second mixture comprising amlodipine benzoate;
  (iv) combining the second mixture with a third mixture comprising sucralose, silicon dioxide, hydroxypropyl methylcellulose, simethicone, a citrate buffer, and optionally a flavoring agent to obtain the amlodipine benzoate suspension;
the amlodipine benzoate suspension comprising:
  a) amlodipine benzoate in an amount corresponding to 1.0 mg/ml amlodipine freebase;
  b) about 3 mM of a citrate buffer;
  c) about 0.2 mg/ml to about 5.0 mg/ml of sodium benzoate;
  d) about 0.7 mg/mL sucralose;
  e) about 0.5 mg/ml of silicon dioxide;
  f) about 7.5 mg/ml of hydroxypropyl methylcellulose;
  g) about 0.5 mg/ml simethicone;
  h) about 1.0 mg/ml of polysorbate 80; and
  i) water.

In some embodiments of a method of preparing an amlodipine benzoate suspension, the aqueous mixture further comprises a first portion of polysorbate 80.

In some embodiments of a method of preparing amlodipine benzoate, the polysorbate 80 is added to the aqueous mixture of step (i) and mixed prior to the addition of amlodipine besylate. This surfactant addition prior to the addition of amlodipine besylate minimizes the potential for amlodipine to adhere to metal containers such as those made of stainless steel.

In some embodiments of a method of preparing an amlodipine benzoate suspension, the aqueous mixture comprising the amlodipine besylate and polysorbate 80 is mixed prior to the addition of sodium benzoate in step (ii). This mixing ensures an even dispersion of the amlodipine besylate and polysorbate 80. In some embodiments of a method of preparing an amlodipine benzoate suspension, the mixing prior to the addition of sodium benzoate in step (ii) is performed for between about 1 minute and about 10 minutes. In some embodiments of a method of preparing an amlodipine benzoate suspension, the mixing prior to the addition of sodium benzoate in step (ii) is performed for about 1 minute, about 2 minutes, about 3 minutes, about 4 minutes, about 5 minutes, about 6 minutes, about 7 minutes, about 8 minutes, about 9 minutes, or about 10 minutes.

In some embodiments of a method of preparing an amlodipine benzoate suspension, the first mixture comprising amlodipine besylate, polysorbate 80, and sodium benzoate is mixed before being subjected to ultrasonic agitation.

In some embodiments of a method of preparing an amlodipine benzoate suspension, the first mixture comprising amlodipine besylate, polysorbate 80, and sodium benzoate is mixed while being subjected to ultrasonic agitation.

In some embodiments of a method of preparing an amlodipine benzoate suspension, the first mixture comprising amlodipine besylate, polysorbate 80, and sodium benzoate is mixed after being subjected to ultrasonic agitation.

In some embodiments of a method of preparing an amlodipine benzoate suspension, the mixing after being subjected to ultrasonic agitation is performed for between about 1 minute and about 30 minutes. In some embodiments of a method of preparing an amlodipine benzoate suspension, the mixing after being subjected to ultrasonic agitation is performed for between about 10 minutes and about 30 minutes. In some embodiments of a method of preparing an amlodipine benzoate suspension, the mixing after being subjected to ultrasonic agitation is performed for about 10 minutes, about 11 minute, about 12 minutes, about 13 minutes, about 14 minutes, about 15 minutes, about 16 minutes, about 17 minutes, about 18 minutes, about 19 minutes, about 20 minutes, about 21 minute, about 22 minutes, about 23 minutes, about 24 minutes, about 25 minutes, about 26 minutes, about 27 minutes, about 28 minutes, about 29 minutes, or about 30 minutes.

In some embodiments of a method of preparing an amlodipine benzoate suspension, the frequency of the ultrasonic agitation is between about 20 kHz and about 100 kHz. In some embodiments of a method of preparing an amlodipine benzoate suspension, the frequency of the ultrasonic agitation is about 20 kHz. In some embodiments of a method of preparing an amlodipine benzoate suspension, the frequency of the ultrasonic agitation is about 40 kHz. In some embodiments of a method of preparing amlodipine benzoate, the frequency of the ultrasonic agitation is modulated about ±1 kHz around the desired frequency.

In some embodiments of a method of preparing an amlodipine benzoate suspension, the duration of the ultrasonic agitation is between about 1 minute and 1 hour. In some embodiments of a method of preparing an amlodipine benzoate suspension, the duration of the ultrasonic agitation is about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. In some embodiments of a method of preparing an amlodipine benzoate suspension, the duration of the ultrasonic agitation is between about 5 minutes and 30 minutes. In some embodiments of a method of preparing an amlodipine benzoate suspension, the duration of the ultrasonic agitation is between about 5 minutes and 20 minutes. In some embodiments of a method of preparing an amlodipine benzoate suspension, the duration of the ultrasonic agitation is about 5 minutes. In some embodiments of a method of preparing an amlodipine benzoate suspension, the duration of the ultrasonic agitation is about 10 minutes.

In some embodiments of a method of preparing an amlodipine benzoate suspension, the temperature of the first mixture or the second mixture is not controlled.

In some embodiments of a method of preparing an amlodipine benzoate suspension, the process does not involve the use of any solvent other than water.

In some embodiments of a method of preparing an amlodipine benzoate suspension, the process further comprises adding the second mixture comprising amlodipine benzoate to a third mixture comprising one or more of a buffer, a preservative, a sweetening agent, a suspension agent, an antifoaming agent, water, and a flavoring agent. In some embodiments, the third mixture comprises water.

In some embodiments of a method of preparing an amlodipine benzoate suspension, the process further comprises adding a second portion of polysorbate 80 to the second mixture comprising amlodipine benzoate prior to step (iv).

In some embodiments of a method of preparing an amlodipine benzoate suspension, the process further comprises adding water quantum satis thereby forming the amlodipine benzoate suspension.

Methods of Treatment

Provided herein, in one aspect, are methods of treatment comprising administration of the amlodipine liquid formulations described herein to a subject. In some embodiments, the amlodipine liquid formulations described herein treat hypertension in a subject. Hypertension as used herein includes both primary (essential) hypertension and secondary hypertension. In certain instances, hypertension is classified in cases when blood pressure values are greater than or equal to 140/90 (systolic/diastolic) mm Hg in a subject. In certain instances, the amlodipine liquid formulations described herein treat a subject having a blood pressure values are greater than or equal to 140/90 mm Hg. In certain instances, the amlodipine liquid formulations described herein treat primary (essential) hypertension in a subject. In other instances, the amlodipine liquid formulations described herein treat secondary hypertension in a subject.

In other embodiments, the amlodipine liquid formulations described herein treat prehypertension in a subject. Prehypertension as used herein refers to cases where a subject's blood pressure is elevated above normal but not to the level considered to be hypertension. In some instances, prehypertension is classified in cases when blood pressure values are 120-139/80-89 mm Hg. In certain instances, the amlodipine liquid formulations described herein treat a subject having blood pressure values of 120-139/80-89 mm Hg.

In yet other embodiments, the amlodipine liquid formulations described herein are prophylactically administered to subjects suspected of having, predisposed to, or at risk of developing hypertension. In some embodiments, the administration of amlodipine liquid formulations described herein allow for early intervention prior to onset of hypertension. In certain embodiments, upon detection of a biomarker, environmental, genetic factor, or other marker, the amlodipine liquid formulations described herein are prophylactically administered to subjects.

In further embodiments, the amlodipine liquid formulations described herein treat Coronary Artery Disease (CAD). In some embodiments, the amlodipine liquid formulations described herein treat chronic stable angina. In some embodiments, the amlodipine liquid formulations described herein treat vasospastic angina (Prinzmetal's or Variant angina). In some embodiments, the amlodipine liquid formulations described herein treat angiographically documented coronary artery disease in patients without heart failure or an ejection fraction <40%.

Dosing

In one aspect, the amlodipine liquid formulations are used for the treatment of diseases and conditions described herein. In addition, a method for treating any of the diseases or conditions described herein in a subject in need of such treatment, involves administration of amlodipine liquid formulations in therapeutically effective amounts to said subject.

Dosages of amlodipine liquid formulations described can be determined by any suitable method. Maximum tolerated doses (MTD) and maximum response doses (MRD) for amlodipine can be determined via established animal and human experimental protocols as well as in the examples described herein. For example, toxicity and therapeutic efficacy of amlodipine can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Amlodipine dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given amlodipine liquid formulation that corresponds to such an amount varies depending upon factors such as the particular amlodipine salt or form, disease condition and its severity, the identity (e.g., weight, sex) of the subject or host in need of treatment, but can nevertheless be determined according to the particular circumstances surrounding the case, including, e.g., the specific agent being administered, the liquid composition type, the condition being treated, and the subject or host being treated.

In some embodiments, the amlodipine liquid formulations described herein are provided in a dose per day from about 0.01 mg to 100 mg, from about 0.1 mg to about 80 mg, from about 1 to about 60, from about 2 mg to about 40 mg of amlodipine. In certain embodiments, the amlodipine liquid formulations described herein are provided in a daily dose of about 0.01 mg, about 0.05 mg, about 0.1 mg, about 0.2 mg, about 0.4 mg, about 0.6 mg, about 0.8 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 76, mg, about 80 mg, about 85 mg, about 90 mg or about 100 mg, or any range derivable therein. In certain instances, the amlodipine liquid formulations described herein are provided in a dose per day of about 1 mg. In certain instances, the amlodipine liquid formulations described herein are provided in a dose per day of about 2 mg. In certain instances, the amlodipine liquid formulations described herein are provided in a dose per day of about 3 mg. In certain instances, the amlodipine liquid formulations described herein are provided in a dose per day of about 4 mg. In certain instances, the amlodipine liquid formulations described herein are provided in a dose per day of about 5 mg. In certain instances, the amlodipine liquid formulations described herein are provided in a dose per day of about 6 mg. In certain instances, the amlodipine liquid formulations described herein are provided in a dose per day of about 7 mg. In certain instances, the amlodipine liquid formulations described herein are provided in a dose per day of about 8 mg. In certain instances, the amlodipine liquid formulations described herein are provided in a dose per day of about 9 mg. In certain instances, the amlodipine liquid formulations described herein are provided in a dose per day of about 10 mg. In certain instances, the amlodipine liquid formulations described herein are provided in a dose per day of about 11 mg. In certain instances, the amlodipine liquid formulations described herein are provided in a dose per day of about 12 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the amlodipine liquid formulations described herein are from about 0.01 to about 1.0 mg/kg per body weight. In one embodiment, the daily dosages appropriate for the amlodipine liquid formulations are from about 0.02 to about 0.8 mg/kg amlodipine per body weight. In another embodiment, the daily dosage appropriate for the amlodipine liquid formulations are from about 0.05 to about 0.6 mg/kg per body weight. In another embodiment, the daily dosage appropriate for the amlodipine liquid formulations is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, or about 0.60 mg/kg.

In other embodiments, the amlodipine liquid formulations are provided at the maximum tolerated dose (MTD) for amlodipine. In other embodiments, the amount of the amlodipine liquid formulations administered is from about 10% to about 90% of the maximum tolerated dose (MTD), from about 25% to about 75% of the MTD, or about 50% of the MTD. In particular embodiments, the amount of the amlodipine liquid formulations administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for amlodipine.

In further embodiments, the amlodipine liquid formulations are provided in a dosage that is similar, comparable or equivalent to a dosage of a known amlodipine tablet formulation. In other embodiments, the amlodipine liquid formulations are provided in a dosage that provides similar, comparable or equivalent pharmacokinetic parameters (e.g., AUC, $C_{max}$, $T_{max}$, $C_{min}$, $T_{1/2}$) as a dosage of a known amlodipine tablet formulation. Similar, comparable or equivalent pharmacokinetic parameters, in some instances, refer to within 80% to 125%, 80% to 120%, 85% to 125%, 90% to 110%, or increments therein, of the given values. It should be recognized that the ranges can, but need not be symmetrical, e.g., 85% to 105%.

Administration

Administration of an amlodipine liquid formulation is at a dosage described herein or at other dose levels and formulations determined and contemplated by a medical practitioner. In certain embodiments, the amlodipine liquid formulations described herein are administered for prophylactic and/or therapeutic treatments. In certain therapeutic applications, the amlodipine liquid formulations are administered to a patient already suffering from a disease, e.g., hypertension, in an amount sufficient to cure the disease or at least partially arrest or ameliorate the symptoms, e.g., lower blood pressure. Amounts effective for this use depend on the severity of the disease, previous therapy, the patient's health status, weight, and response to the amlodipine formulations, and the judgment of the treating physician. Therapeutically effective amounts are optionally determined by methods including, but not limited to, a dose escalation clinical trial.

In prophylactic applications, the amlodipine liquid formulations described herein are administered to a patient susceptible to or otherwise at risk of a particular disease, e.g., hypertension. Such an amount is defined to be a "prophylactically effective amount or dose." In this use, the precise amounts also depend on the patient's state of health, weight, and the like. When used in a patient, effective amounts for this use will depend on the risk or susceptibility of developing the particular disease, previous therapy, the patient's health status and response to the amlodipine formulations, and the judgment of the treating physician.

In certain embodiments wherein the patient's condition does not improve, upon the doctor's discretion the administration of an amlodipine liquid formulations described herein are administered chronically, that is, for an extended period of time, including throughout the duration of the patient's life in order to ameliorate or otherwise control or limit the symptoms of the patient's disease. In other embodiments, administration of an amlodipine liquid formulation continues until complete or partial response of a disease.

In certain embodiments wherein a patient's status does improve, the dose of an amlodipine liquid formulation being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, amlodipine liquid formulations described herein are administered chronically. For example, in some embodiments, an amlodipine liquid formulation is administered as a continuous dose, i.e., administered daily to a subject. In some other embodiments, amlodipine liquid formulations described herein are administered intermittently (e.g. drug holiday that includes a period of time in which the formulation is not administered or is administered in a reduced amount).

In some embodiments, the amlodipine liquid formulation is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, an amlodipine liquid formulation is administered orally to a subject who is in a fasted state for at least 8 hours. In other embodiments, an amlodipine liquid formulation is administered to a subject who is in a fasted state for at least 10 hours. In yet other embodiments, an amlodipine liquid formulation is administered to a subject who is in a fasted state for at least 12 hours. In other embodiments, an amlodipine liquid formulation is administered to a subject who has fasted overnight.

In other embodiments, the amlodipine liquid formulation is administered to a subject who is in a fed state. A fed state refers to a subject who has taken food or has had a meal. In certain embodiments, an amlodipine liquid formulation is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain instances, an amlodipine liquid formulation is administered to a subject in a fed state 30 minutes post-meal. In other instances, an amlodipine liquid formulation is administered to a subject in a fed state 1 hour post-meal. In yet further embodiments, an amlodipine liquid formulation is administered to a subject with food.

In further embodiments described herein, an amlodipine liquid formulation is administered at a certain time of day for the entire administration period. For example, an amlodipine liquid formulation can be administered at a certain time in the morning, in the evening, or prior to bed. In certain instances, an amlodipine liquid formulation is administered in the morning. In other embodiments, an amlodipine liquid formulation can be administered at different times of the day for the entire administration period. For example, an amlodipine liquid formulation can be administered on 8:00 am in the morning for the first day, 12 pm noon for the next day or administration, 4 pm in the afternoon for the third day or administration, and so on.

Combinations

The treatment of certain diseases or conditions (e.g., hypertension, heart failure, myocardial infarction and the like) in a subject with an amlodipine liquid formulation described herein encompass additional therapies and treatment regimens with other agents in some embodiments. Such additional therapies and treatment regimens can include another therapy, e.g., additional anti-hypertensives, for treatment of the particular disease or condition in some embodiments. Alternatively, in other embodiments, additional therapies and treatment regimens include other agents used to treat adjunct conditions associated with the disease or condition or a side effect from the amlodipine liquid formulation in the therapy.

Additional agents for use in combination with an amlodipine liquid formulation described herein include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dihydropyridines such as nifedipine, etc., diltiazem, verapamil and the like), angiotensin II receptor antagonists (saralasin, losartan, eprosartin, irbesartan, valsartan, and the like), other ACE inhibitors (enalapril, captopril, quinapril, ramipril, lisinopril, zofenopril, and the like), aldosterone antagonists (eplerenone, spironolactone and the like), vasodilators (hydralazine and the like) and alpha-2 agonists (clonidine, moxonidine, guanabenz and the like).

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as amlodipine is directed to the treatment and/or the amelioration of, reversal of, or stabilization of the symptoms of hypertension described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an amlodipine formulation, can include, but is not limited to, providing an amlodipine formulation into or onto the target tissue; providing an amlodipine formulation systemically to a patient by, e.g., oral administration whereby the therapeutic reaches the target tissue or cells. "Administering" a formulation may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology. A patient can be a human suffering from hypertension, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a formulation of the present disclosure may be used to inhibit, block, or reverse the activation, migration, or proliferation of cells or to effectively treat hypertension or ameliorate the symptoms of hypertension.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

The terms "precipitate," "precipitates," or "precipitation" as used herein, refers to the creation of a new solid phase comprising one or more chemical entities from solution. Those of ordinary skill in the art will understand and appreciate that the solid phase may exist in crystalline and/or amorphous forms and that crystalline forms may include, but are not limited to, polymorphs, cocrystals, ionic cocrystals, ionic cocrystal solvates, salts, solvated salts and solvates.

The terms "substantially precipitate," "substantially precipitates" or "substantial precipitation" as used herein, refers to an amount of precipitation that is detectable, directly or indirectly, by techniques known to a person of ordinary skill in the art. Examples of techniques may include, but are not limited to, visual inspection of solutions to determine changes in solution opaqueness/transparency, Focused Beam Reflectance Measurement (FBRM) technology, Infrared Spectroscopy, Raman Spectroscopy, UV spectroscopy and turbidity analysis.

The terms "very slightly soluble" or "practically insoluble" as used herein, refers to a concentration of less than about 0.6 mg/mL, preferably of less than about 0.2 mg/mL, and most preferably of less than about 0.05 mg/mL.

EXAMPLES

Example 1: Formation of Amlodipine Salts

Amlodipine salts were prepared according to the formulas in Table 1 and Table 2. The formulations in Table 1 were prepared by adding purified water to a glass container containing a magnetic stir-bar and mixing with an external magnetic stir-plate. The polysorbate 80 was added and allowed to dissolve with mixing for a minimum of 10 minutes. Amlodipine besylate was then added and dispersed in the solution with mixing for a minimum of 10 minutes. The salt forming agent was then added to the suspension and the resulting suspension was mixed for an additional 30 minutes. The amount of the added salt forming agent was approximately 10-fold the amount of amlodipine on a mole basis. A control formulation was prepared to provide a solubility value for amlodipine besylate.

The formulations in Table 2 were prepared by adding purified water to a glass container positioned in an ultrasonic bath. Mixing was initiated with an overhead mixer and impeller. The polysorbate 80 was added and allowed to dissolve with mixing for a minimum of 10 minutes. Amlodipine besylate was then added and dispersed in the solution with mixing for a minimum of 10 minutes. The salt forming agent was then added to the suspension along with a pH adjusting agent if needed, and ultrasonic agitation at 40 kHz was applied for 30 minutes along with overhead mixing.

An aliquot of each suspension was filtered through a 0.45 micron nylon filter and the supernatant analyzed by an HPLC method for amlodipine content. The HPLC method provided separation of amlodipine from other components on a C18 column with a gradient program using mobile phases containing 0.1% trifluoroacetic acid (TFA) in water, and 0.1% TFA in acetonitrile flowing at 1 mL/min. Detection was by UV absorbance at 237 nm. The results are included in Table 1 and Table 2.

TABLE 2

Composition of Amlodipine Salt Batches Prepared by Sonication and Mixing

| Component (g) | 1G | 1H | 1I | 1J | 1K |
| --- | --- | --- | --- | --- | --- |
| Purified water | 100 | 10 | 10 | 100 | 100 |
| Polysorbate 80 | 1.0 | 0.10 | 0.10 | 1.0 | 1.0 |
| Amlodipine besylate | 1.39 | 0.139 | 0.139 | 1.39 | 1.39 |
| Benzoic acid | 4.24 | — | — | — | — |
| Sodium hydroxide (5N solution) | 8.25 | — | — | — | — |
| (1S)-(+)-10-Camphorsulfonic acid | — | 0.569 | — | — | — |
| 1-Hydroxy-2-naphthoic acid | — | — | 0.461 | — | — |
| Pamoic acid, disodium | — | — | — | 10.59 | — |
| Terephthalic acid | — | — | — | — | 4.07 |
| Amlodipine content in supernatant (mg/mL) | 0.73 | 0.63 | 2.58 | 1.42 | 3.84 |

Batches 1A-1F had different amlodipine content in the supernatants than the amlodipine besylate control indicating formation of new salt forms. The remaining suspension from batches 1A, 1B, 1E, and 1F (showing lower amlodipine content than amlodipine besylate) was filtered through Whatman #1 filter paper and the solids collected, rinsed twice with purified water, then allowed to dry at ambient conditions for one hour. Aliquots of each solid were weighed into 15 mL polypropylene centrifuge tubes in duplicate except for batch 1A which was a single determination. Purified water was added to each tube and the pH of the resulting suspension adjusted to 5.3 with anhydrous citric acid or anhydrous sodium citrate powder as needed. A control was also prepared in duplicate containing only purified water and amlodipine besylate at pH 5.3. The tubes were capped, covered in foil to block light, and allowed to tumble end-over-end at ambient temperature for 66 hours. The suspensions were then filtered through 0.45 micron nylon filters and the resulting filtrates analyzed by HPLC for amlodipine content. The contents of each tube, and the resulting amlodipine solubilities are presented in Table 3.

TABLE 1

Composition of Amlodipine Salt Batches Prepared by Mixing

| Component (g) | Control | 1A | 1B | 1C | 1D | 1E | 1F |
| --- | --- | --- | --- | --- | --- | --- | --- |
| Purified water | 500 | 10 | 10 | 100 | 10 | 100 | 100 |
| Polysorbate 80 | 5.0 | 0.10 | 0.10 | 1.0 | 0.10 | 1.0 | 1.0 |
| Amlodipine besylate | 6.95 | 0.139 | 0.139 | 1.39 | 0.139 | 1.39 | 1.39 |
| (1S)-(+)-10-Camphorsulfonic acid | — | 0.568 | — | — | — | — | — |
| 1-Hydroxy-2-naphthoic acid | — | — | 0.461 | — | — | — | — |
| 1,5-Naphthalene disulfonic acid, disodium | — | — | — | 8.60 | — | — | — |
| Nicotinic acid, sodium | — | — | — | — | 0.358 | — | — |
| Pamoic acid, disodium | — | — | — | — | — | 10.60 | — |
| Terephthalic acid | — | — | — | — | — | — | 4.07 |
| Amlodipine content in supernatant (mg/mL) | 4.80 | 0.63 | 2.44 | 7.11 | 9.04 | 1.70 | 2.26 |

TABLE 3

Soluble Amlodipine in Isolated Solids

| | Control Tube 1/2 | 1A Tube 1 | 1B Tube 1/2 | 1E Tube 1/2 | 1F Tube 1/2 |
|---|---|---|---|---|---|
| Purified water (mL) | 10/10 | 10 | 10/10 | 10/10 | 10/10 |
| Amlodipine besylate (mg) | 49.8/53.1 | — | — | — | — |
| Isolated solids added (mg) | — | 54.8 | 99.4/100.5 | 100.0/104.6 | 111.2/131.1 |
| pH | 5.38/5.26 | 5.33 | 5.26/5.25 | 5.40/5.32 | 5.27/5.32 |
| Soluble amlodipine (μg/mL) | 1078/1076 | 950 | 0.27/0.21 | 0.33/0.22 | 9.4/5.6 |

Example 2: Effect of Polysorbate 80 on the Formation of Amlodipine Benzoate in Stainless Steel Containers The benzoate salt of amlodipine was prepared in stainless steel containers in the absence and presence of varying amount of polysorbate 80. Amlodipine besylate has been reported to adsorb/adhere to stainless steel surfaces with one report indicating that 0.1% polysorbate 80 inhibits this adsorption/adherence in solution. The batches were prepared using the ingredients as specified in Table 4. The batch with no polysorbate (2A) was prepared by adding the purified water to a stainless steel vessel and initiating mixing with an overhead mixer and stainless steel stirrer shaft and blade. Citric acid was added and dissolved, then amlodipine besylate was added. The suspension was mixed for ~5 minutes then sodium benzoate was added.

Large crystals promptly formed in the suspension and solid material was observed to stick to, and coat, the stir-shaft and impeller as well as the inner surface of the stainless steel vessel. No further processing or sampling was undertaken.

The polysorbate containing batches (2B-2F) were prepared as 7.5% concentrates by adding 4.50 liters of purified water to a stainless steel sonication tank with an overhead mixer and stainless steel stirrer shaft and blade. Mixing was initiated and the polysorbate 80 was added. The polysorbate container was rinsed with 0.25 L purified water and the rinse was added to the tank. The solution was stirred for 10 minutes and the amlodipine besylate was added to the tank. The amlodipine besylate container was rinsed with 0.25 L purified water and the rinse was added to the tank. The solution/suspension was stirred for 10 minutes then sonication was initiated (40 kHz frequency, 280 watts) and sodium benzoate was added to the tank. The sonication was discontinued after 10 minutes and the mixing continued for an additional 20 minutes. No solid material was observed to adhere to the container or the mixing shaft and blade. Samples of the suspension were taken periodically, filtered through a 0.45 micron nylon filter and the supernatant analyzed by the HPLC method in Example 1 for amlodipine content. Additional samples of the suspension were taken after the sonication and subsequent 20 minute stirring were completed. The samples were evaluated for particle size with a Malvern Mastersizer S using a 5 mg/mL sodium benzoate in water dispersant.

TABLE 4

Amlodipine Salt Batches Evaluating Polysorbate Content

| Components (grams) | 2A | 2B | 2C | 2D | 2E | 2F |
|---|---|---|---|---|---|---|
| Purified water | 1350 | 5000 | 5000 | 5000 | 5000 | 5000 |
| Citric acid, anhydrous | 0.825 | — | — | — | — | — |
| Polysorbate 80 | 0 | 5.00 | 15.0 | 25.0 | 30.0 | 66.7 |
| Amlodipine besylate | 2.08 | 92.6 | 92.6 | 92.6 | 92.6 | 92.6 |
| Sodium benzoate | 7.50 | 333.6 | 333.6 | 333.6 | 333.6 | 333.6 |
| Results Particle size (μm) | | | | | | |
| D10 | — | 5 | 3 | 3 | 3 | 3 |
| D50 | — | 29 | 13 | 14 | 13 | 14 |
| D90 | — | 56 | 32 | 43 | 34 | 33 |

The concentration of amlodipine in solution over time for batches 2B-2F are given in FIG. 1.

Example 3: Effect of Sonication on the Formation of Amlodipine Benzoate

The benzoate salt of amlodipine was prepared with overhead stirring (Formulation 3A), magnetic stir-bar stirring (Formulation 3B), and by sonication (40 kHz) with overhead stirring (Formulation 3C). The resulting suspensions were then used to prepare sweetened, suspended, formulations. The compositions of the three formulations are given in Table 5.

TABLE 5

Amlodipine Formulations Prepared by Different Mixing Methods

| | Formulation | | |
|---|---|---|---|
| | 3A | 3B | 3C |
| Salt Formation Step (grams) | | | |
| Purified water-I | 300 | 100 | 5000 |
| Polysorbate 80 | 3.00 | 1.00 | 50.0 |
| Amlodipine besylate | 4.17 | 1.39 | 69.5 |
| Sodium benzoate | 15.0 | 5.00 | 250.0 |
| Formulation Step (grams) | | | |
| Purified water-II | 2433 | 812 | 487 |
| Citric acid, anhydrous | 0.93 | 0.310 | 0.186 |
| Sodium citrate, anhydrous | 1.08 | 0.361 | 0.216 |
| Simethicone 30% w/w powder | 1.50 | 0.50 | 0.300 |
| Sucralose | 2.10 | 0.70 | 0.420 |
| Colloidal silicon dioxide | 1.50 | 0.50 | 0.30 |
| Hypromellose | 22.5 | 7.50 | 4.50 |
| Purified water III | q.s. 3 L | q.s. 1 L | q.s. 0.6 L |
| Results | | | |
| Particle size (μm) | | | |
| D10 | 16 | 12 | 3 |
| D50 | 46 | 32 | 13 |
| D90 | 194 | 96 | 29 |

The amlodipine salts were prepared by adding the Purified water-I to a stainless steel vessel (Formulations 3A, 3B), or sonication tank (Formulation 3C). Mixing was initiated and the polysorbate 80, then amlodipine besylate, was added with 5 minutes of mixing following each addition. The sodium benzoate was added, and sonication was initiated for Formulation 3C. Mixing was continued for 30 minutes after the sodium benzoate addition for all batches, and sonication for 3C was continued for 10 minutes after the sodium benzoate addition.

Purified water II was added to a glass vessel for each of the formulations and magnetic stir bar mixing was initiated for each. The following ingredients were added to each vessel with 5 minutes of mixing between each addition; citric acid, sodium citrate, simethicone 30% solid (NuSil Med-342P), sucralose, colloidal silicon dioxide (Cab-O-Sil M-5P), and hypromellose (Benecel K1500). The magnetic stir bar was removed, and high shear mixing was applied for 2 minutes to disperse and hydrate the hypromellose. The full contents of the suspension from the salt formation step for Formulations 3A and 3B and 64.3 grams of the suspension from Formulation 3C (containing the salt equivalent of 0.832 g amlodipine besylate) were added to the glass vessels and high shear mixing was applied for 1 minute to disperse the amlodipine benzoate particles. The formulations were brought to their respective final volume with Purified water III, and mixed until uniform.

Samples of each suspension were taken and evaluated for particle size with a Malvern Mastersizer S using a 5 mg/mL sodium benzoate in water dispersant. The results are presented in Table 5.

Figure 2:
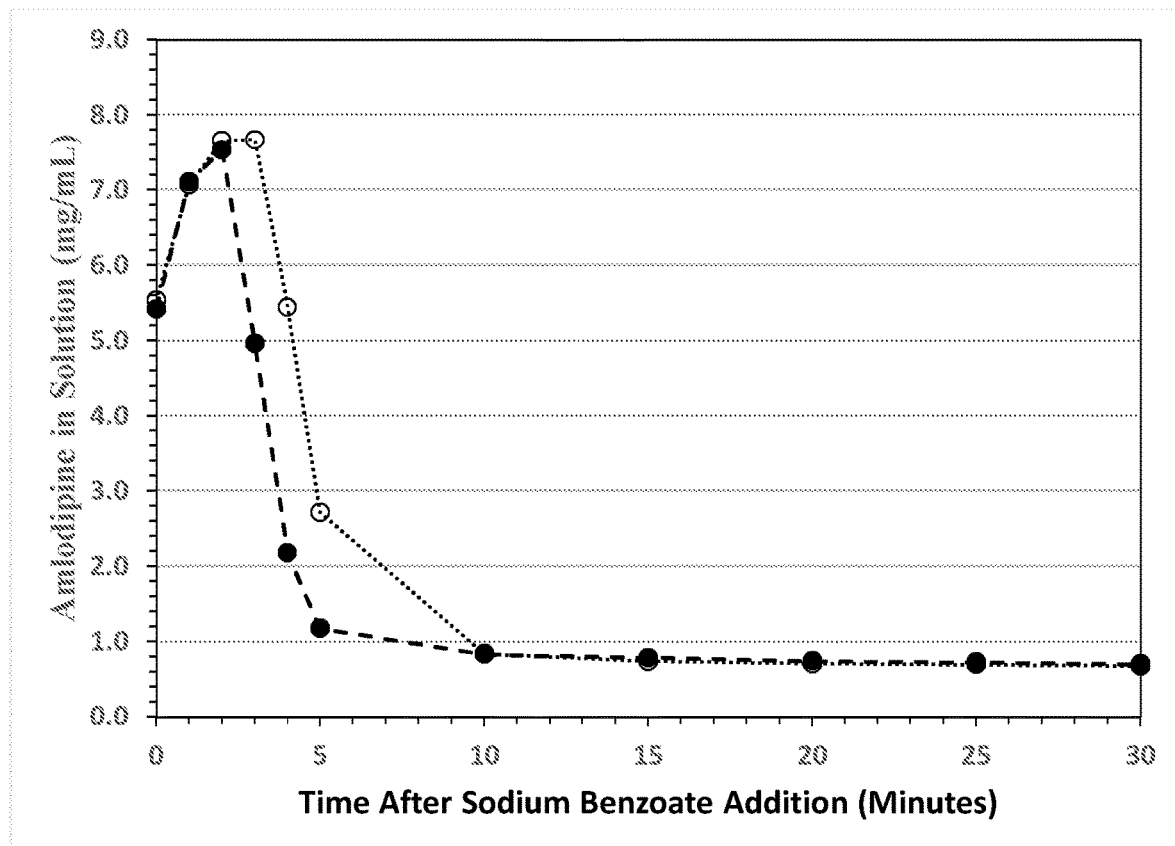
FIG. 2 shows the amount of amlodipine remaining in solution over time when sonicated for 10 minutes at 25 kHz (○) and 40 kHz (•) frequency.

Example 4: Effect of Sonication Frequency on the Formation of Amlodipine Benzoate A batch of amlodipine benzoate salt (4A) was prepared containing the same composition as batch 2F. The preparation procedure was the same as for batch 2F with the exception that the sonication frequency was 20 kHz. Samples of the suspension were taken periodically, filtered through a 0.45 micron nylon filter and the supernatant analyzed by the HPLC method in Example 1 for amlodipine content. Additional samples of the suspension were taken after the sonication and subsequent 20 minute stirring, and the samples were evaluated for particle size with a Malvern Mastersizer S using a 5 mg/mL sodium benzoate in water dispersant. The measured particle size of batch 4A was D10=4 micron, D50=19 micron, and D90=55 micron and the particle size of batch 2F was D10=3 micron, D50=14 micron, and D90=33 micron. The concentration of soluble amlodipine in solution over time for batches 2F and 4A are given in FIG. 2.

Example 5: Effect of Sonication Duration on the Formation of Amlodipine Benzoate Batches of amlodipine benzoate salt were prepared containing the components as shown in Table 6. The batches were prepared according to the procedure used for the preparation of batch 2F with the exception that the sonication was conducted for 10 minutes for batch 5A and for 30 minutes for batch 5B. Samples of each suspension were taken periodically during the procedure, filtered through a 0.45 micron nylon filter and the supernatant analyzed by the HPLC method in Example 1 for amlodipine content. The concentration of soluble amlodipine in solution over time for batches 5A and 5B was essentially the same.

TABLE 6

Amlodipine Salt Batches Evaluating Sonication Duration

| | Batch | |
|---|---|---|
| Components (grams) | 5A | 5B |
| Purified water | 5000 | 5000 |
| Polysorbate 80 | 50.0 | 50.0 |
| Amlodipine besylate | 69.5 | 69.5 |
| Sodium benzoate | 50.0 | 50.0 |
| Sonication duration | 10 min | 30 min |

Example 6: Effect of Solution Concentration on the Formation of Amlodipine Benzoate Amlodipine benzoate salt was prepared under conditions where the concentrations of ingredients was varied to simulate preparation of the salt under various concentrate conditions. The compositions of the batches are given in Table 7 along with batches 2F and 3C. The batches were prepared according to the procedure used for batch 2F. Samples of the suspension from batch 6B was taken and evaluated for particle size with a Malvern Mastersizer S using a 5 mg/mL sodium benzoate in water dispersant.

TABLE 7

Composition and Particle Sizes of Amlodipine Salt Batches Made as Concentrates

| | Batch | | | |
|---|---|---|---|---|
| | 6A | 2F | 3C | 6B |
| Component (grams) | | | | |
| Purified water | 5000 | 5000 | 5000 | 5000 |
| Polysorbate 80 | 100.0 | 66.7 | 50.00 | 5.00 |
| Amlodipine besylate | 139.0 | 92.6 | 69.5 | 6.95 |
| Sodium benzoate | 500.0 | 333.3 | 250.0 | 25.0 |

TABLE 7-continued

Composition and Particle Sizes of Amlodipine
Salt Batches Made as Concentrates

|  | Batch | | | |
| --- | --- | --- | --- | --- |
|  | 6A | 2F | 3C | 6B |
| Condition/Result | | | | |
| Concentrate volume % | 5 | 7.5 | 10 | 100 |
| Particle size (μm) | | | | |
| D10 | — | 3 | 3 | 8 |
| D50 | — | 14 | 13 | 30 |
| D90 | — | 33 | 29 | 72 |

Example 7: Amlodipine Salt Formation when Varying the Polysorbate Addition

Amlodipine salts were prepared as 10% concentrates containing the compositions shown in Table 8. Batch 7A was prepared by adding 41 kg purified water to a 22 gallon sonication tank with an overhead mixer and stainless steel stirrer shaft and blade. Mixing was initiated and polysorbate 80 [Aliquot 1] was added. The polysorbate container was rinsed with 0.5 L purified water and the rinse was added to the tank. The solution was stirred for 10 minutes and the amlodipine besylate was added to the tank. The amlodipine besylate container was rinsed with 0.5 L purified water and the rinse was added to the tank. The solution/suspension was stirred for 10 minutes then sonication was initiated (40 kHz frequency with ±1 kHz modulation, 1500 watts) and sodium benzoate was added to the tank. The sonication was discontinued after 10 minutes. Mixing continued for an additional 20 minutes after the sonication was discontinued, then polysorbate 80 [Aliquot 2] was added. The polysorbate container was rinsed with 0.5 L purified water and the rinse was added to the tank. The suspension was mixed for an additional 10 minutes.

Batch 7B was prepared by adding 290 g purified water to a 600 mL glass beaker mounted in a sonication tank. An overhead mixer with a PTFE stirrer shaft and blade was positioned to mix the solution in the beaker Mixing was initiated and polysorbate 80 [Aliquot 1] was added. The polysorbate container was rinsed with 5 mL purified water and the rinse was added to the beaker. The solution was stirred for 10 minutes and the amlodipine besylate was added to the beaker. The amlodipine besylate container was rinsed with 5 mL purified water and the rinse was added to the beaker. The solution/suspension was stirred for 10 minutes then sonication was initiated (40 kHz frequency, 280 watts) and sodium 2-napthalene sulfonate was added to the beaker. The sonication was discontinued after 10 minutes and the mixing was continued for an additional 20 minutes.

TABLE 8

Composition of Amlodipine Salt Batches
Varying Polysorbate Addition

|  | Batch | |
| --- | --- | --- |
| Component (grams) | 7A | 7B |
| Purified water | 42500 | 300 |
| Polysorbate 80 [Aliquot 1] | 255.0 | 0.30 |
| Amlodipine besylate | 591 | 4.16 |
| Sodium benzoate | 2125 | — |

TABLE 8-continued

Composition of Amlodipine Salt Batches
Varying Polysorbate Addition

|  | Batch | |
| --- | --- | --- |
| Component (grams) | 7A | 7B |
| Sodium 2-napthalene sulfonate | — | 3.39 |
| Polysorbate 80 [Aliquot 2] | 170.0 | — |

Example 8: Stability of Amlodipine Formulations

Formulations were prepared containing Amlodipine according to the compositions in Table 9, using the amlodipine salts prepared in Example 7. Each formulation contained amlodipine equivalent to 1.39 mg/mL of amlodipine besylate.

Formulations 8A-C were prepared by adding the ingredients to a volume of purified water that was about 80% of the final volume of the formulation. The suspending agent, hypromellose or xanthan gum, was added last and high shear mixing was applied to disperse and hydrate the suspending agent. The appropriate amount of batch 7A was added to each and the formulations were brought to their final volume with purified water. The pH of each formulation was measured.

Formulation 8D was prepared by heating to 75° C., a volume of purified water that was about 50% of the final volume of the formulation. The magnesium aluminum silicate was added and mixed for 45 minutes. The sucrose and sorbitol were added to the hot suspension and dissolved. The formulation was then cooled to ambient temperature and the sodium citrate, simethicone, microcrystalline cellulose, and 0.31 mg/mL citric acid were added. The appropriate amount of batch 7A was added and the formulation was brought to final volume with purified water. The pH was measured and adjusted to 5.3 with additional citric acid.

Formulations 8E was prepared using purified water in an amount that was about 65% the final volume of the formulation. The Carbopol was added and dissolved, followed by citric acid, sodium citrate (0.36 mg/mL), xylitol, simethicone and silicon dioxide. The appropriate amount of batch 7A was added and the formulation was brought to final volume with purified water. The pH was measured and adjusted to 5.3 with additional sodium citrate.

Formulation 8F was prepared using purified water in an amount that was about 40% of the final volume of the formulation. Citric acid (0.31 mg/mL), sodium citrate, sucralose, maltitol, simethicone and microcrystalline cellulose were added. Methylcellulose was then added and high shear mixing applied to disperse and hydrate the cellulose. The suspension was then mixed for 15 minutes to allow for dissipation of entrapped air. The appropriate amount of batch 7A was added and the formulation was brought to final volume with purified water. The pH was measured and adjusted to 5.3 with additional citric acid.

Formulation 8G was prepared by dissolving 0.27 g polysorbate 80 in 240 g purified water with mixing in a beaker. The polysorbate container was rinsed with 5 mL water and the rinse was added to the beaker. The following ingredients were then added individually with mixing; citric acid, sodium citrate, sodium benzoate, sucralose, simethicone and colloidal silicon dioxide. Hypromellose was then added and the suspension was subjected to high shear mixing to disperse and hydrate the hypromellose. A 30.78 gram aliquot of batch 7B was added to the beaker and additional purified water was added to bring the formulation to a final volume of 300 mL. The formulation was mixed well.

Each formulation was dispensed into screw-capped high density polyethylene (HDPE) bottles and stored at both 5±5° C. and 25±5° C. for formulations 8A-8F and at both 25° C. and 40±5° C. for formulation 8G. Samples were removed periodically and analyzed by a stability indicating high performance liquid chromatography (HPLC) method for content of amlodipine and any degradants.

The HPLC method provided separation of amlodipine, amlodipine degradants and formulation components on a C18 column with a gradient program using mobile phases containing 0.1% trifluoroacetic acid (TFA) in water, and 0.1% TFA in acetonitrile flowing at 1 mL/min. Detection was by UV absorbance at 237 nm for amlodipine and its degradants. Any unknown impurities were reported by their relative retention time (RRT) to amlodipine.

TABLE 9

Composition of Amlodipine Formulations for Stability Assessment

| Component | 8A | 8B | 8C | 8D | 8E | 8F | 8G |
|---|---|---|---|---|---|---|---|
| Amlodipine[a] | 1.00 | 1.00 | 1.00 | 1.00 | 1.00 | 1.00 | 1.00 |
| Polysorbate 80 | 1.00 | 1.00 | 1.00 | 1.00 | 1.00 | 1.00 | 1.00 |
| Sodium benzoate | 5.00 | 5.00 | 5.00 | 5.00 | 5.00 | 5.00 | 1.00 |
| Sodium 2-napthalene sulfonate | — | — | — | — | — | — | 1.13 |
| Acetic acid | 0.26 | — | — | — | — | — | — |
| Citric acid, anhydrous | — | 0.31 | 0.31 | 0.63 | 0.31 | 0.39 | 0.31 |
| Sodium citrate, anhydrous | — | 0.42 | 0.42 | 0.36 | 5.95 | 0.36 | 0.42 |
| Sucralose | 0.70 | 0.70 | 0.70 | — | — | 0.50 | 0.70 |
| Maltitol syrup (Lycasin 80/55) | — | — | — | — | — | 400 | — |
| Sorbitol | — | — | — | 100 | — | — | — |
| Xylitol | — | — | — | — | 150 | — | — |
| Sucrose | — | — | — | 630 | — | — | — |
| Simethicone 30% w/w powder | 0.50 | 0.50 | 0.50 | 0.50 | 0.50 | 0.50 | 0.50 |
| Colloidal silicon dioxide | 0.50 | 0.50 | 0.50 | — | 0.50 | — | 0.50 |
| Microcrystalline cellulose (Avicel PH101) | — | — | — | 6.0 | — | 5.0 | — |
| Hypromellose (Benecel K1500) | 7.5 | 7.5 | — | — | — | — | 7.5 |
| Xanthan gum | — | — | 1.5 | — | — | — | — |
| Magnesium aluminum silicate (Veegum) | — | — | — | 15 | — | — | — |
| Carbopol 971P | — | — | — | — | 3.0 | — | — |
| Methylcellulose (Methocel A15C) | — | — | — | — | — | 10.0 | — |
| Purified water | q.s. | q.s. | q.s. | q.s. | q.s. | q.s. | q.s. |
| pH | 5.3 | 5.4 | 5.4 | 5.3 | 5.3 | 5.3 | 5.1 |

[a] = equivalent to 1.39 mg/ml Amlodipine besylate

Initial HPLC analysis for amlodipine and the main degradants in the samples (8A-8G) stored at 5±5° C. suggest that one or more of the formulations are stable.

The results of the HPLC analysis for amlodipine and the main degradants in the samples stored at 5±5° C. are provided in Table 10. When stored at 5±5° C., Sample 8G is contemplated to have similar or better stability compared to samples 8A-8F.

TABLE 10

Assay and Primary Degradants Present in the Formulations

| | Formulation | | | | | |
|---|---|---|---|---|---|---|
| | 8A | 8B | 8C | 8D | 8E | 8F |
| Weeks | Amlodipine (% initial) | | | | | |
| Initial | 100.0 | 100.0 | 100.0 | 100.0* | 100.0 | 100.0 |
| 4 | 99.1 | 99.9 | 94.4 | 111.8* | 99.5 | 100.1 |
| 8 | 98.3 | 100.1 | 99.8 | 162.0* | 99.8 | 99.7 |
| 12 | 98.8 | 100.1 | 100.1 | 213.8* | 101.1 | 100.2 |
| 26 | 98.6 | 100.0 | 100.3 | 193.2* | 100.3 | 97.9 |
| 52 | 97.5 | 99.6 | 100.0 | | 99.0 | 99.7 |
| Weeks | Total Impurities (wt % of Amlodipine) | | | | | |
| Initial | 0.13 | 0.06 | 0.05 | 0.27* | 0.18 | 0.15 |
| 4 | 0.28 | 0.12 | 0.08 | 0.35* | 0.27 | 0.08 |
| 8 | 0.51 | 0.17 | 0.11 | 0.13* | 0.19 | 0.08 |
| 12 | 0.70 | 0.20 | 0.14 | 0.22* | 0.25 | 0.10 |

TABLE 10-continued

Assay and Primary Degradants Present in the Formulations

| | Formulation | | | | | |
|---|---|---|---|---|---|---|
| | 8A | 8B | 8C | 8D | 8E | 8F |
| 26 | 0.93 | 0.29 | 0.18 | 0.20* | 0.33 | 0.08 |
| 52 | 1.18 | 0.46 | 0.24 | | 0.66 | 0.42 |

*Formulation 8D was incompatible with the HPLC column, and thus the amlodipine and impurity contents cannot be measured using the HPLC method.

The results of the HPLC analysis for amlodipine and the main degradants in the samples stored at 25±5° C. and 40±5° C. (8G) are provided in Table 11.

TABLE 11

Assay and Primary Degradants Present in the Formulations

| | Formulation | | | | | | | |
|---|---|---|---|---|---|---|---|---|
| | 8A (25° C.) | 8B (25° C.) | 8C (25° C.) | 8D (25° C.) | 8E (25° C.) | 8F (25° C.) | 8G (25° C.) | 8G (40° C.) |
| Weeks | Amlodipine (% initial) | | | | | | | |
| Initial | 100.0 | 100.0 | 100.0 | 100.0* | 100.0 | 100.0 | 100.0 | 100.0 |
| 4 | 97.0 | 99.7 | 100.0 | 105.3* | 95.9 | 98.5 | 98.3 | 97.3 |
| 8 | 96.8 | 98.9 | 97.9 | 119.6* | 95.3 | 97.2 | 99.6 | 96.6 |
| 12 | 96.1 | 98.4 | 98.0 | 183.2* | 93.5 | 97.1 | 99.9 | 94.7 |
| 26 | 93.6 | 96.0 | 95.4 | 174.7* | 88.0 | 93.6 | 102.3 | 86.6 |
| 52 | — | — | — | — | — | — | 100.2 | — |
| Weeks | Total Impurities (wt % of Amlodipine) | | | | | | | |
| Initial | 0.13 | 0.06 | 0.05 | 0.27* | 0.18 | 0.15 | 0.23 | 0.23 |
| 4 | 0.74 | 0.42 | 0.35 | 0.36* | 1.18 | 0.31 | 0.33 | 0.43 |
| 8 | 1.27 | 0.84 | 0.64 | 0.12* | 1.42 | 0.61 | 0.20 | 1.56 |
| 12 | 1.69 | 1.30 | 0.99 | 0.26* | 1.93 | 0.55 | 0.23 | 1.99 |
| 26 | 2.99 | 2.39 | 2.00 | 0.27* | 3.87 | 1.37 | 0.31 | 3.61 |
| 52 | — | — | — | — | — | — | 0.56 | — |

*Formulation 8D was incompatible with the HPLC column, and thus the amlodipine and impurity contents cannot be measured using the HPLC method.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A suspension comprising particles comprising amlodipine benzoate and having a median diameter D50 value of between about 5 μm and about 40 μm as measured by a light scattering particle size analyzer, and the said suspension is made by a process comprising:
    (i) providing an aqueous mixture comprising amlodipine besylate;
    (ii) adding sodium benzoate to the aqueous mixture to form a first mixture; and
    (iii) subjecting the first mixture to ultrasonic agitation at a frequency of between about 20 kHz and about 100 kHz, thereby forming a second mixture comprising amlodipine benzoate.

2. The suspension made by the process of claim 1, wherein the said particles have the D50 value of between about 10 μm and about 20 μm.

3. The suspension made by the process of claim 1, wherein the said particles have a D90 value of between about 20 μm and about 60 μm, and wherein the D90 value refers to a particle diameter, wherein 10% of the volume of the sampled particles have a diameter larger than, and 90% of the volume of the sampled particles have a diameter smaller than said D90 value.

4. The suspension made by the process of claim 1, wherein the aqueous mixture of step (i) further comprises polysorbate 80 acting as a first surfactant.

5. The suspension made by the process of claim 1, wherein the concentration of amlodipine besylate is between about 12 mg/ml and about 20 mg/ml in the aqueous mixture of step (i).

6. The suspension made by the process of claim 1, wherein the concentration of sodium benzoate is between about 40 mg/ml and about 70 mg/ml in the first mixture of step (ii).

7. The suspension made by the process of claim 1, wherein the duration of the ultrasonic agitation in step (iii) is between about 1 minute and 1 hour.

8. The suspension made by the process of claim 1, wherein the duration of the ultrasonic agitation in step (iii) is between about 5 minutes and 30 minutes.

9. The suspension made by the process of claim 1, wherein the aqueous mixture of step (i) does not comprise any solvent other than water.

10. The suspension made by the process of claim 4, wherein the process further comprises adding a second surfactant into the second mixture of step (iii).

11. The suspension made by the process of claim 10, wherein the combined amount of the surfactants is about 0.1 mg/ml to about 2 mg/ml.

12. The suspension made by the process of claim 1, wherein the process further comprises adding the second mixture comprising amlodipine benzoate to a third mixture comprising at least one component selected from a buffer, a preservative, a sweetening agent, a suspension agent, an antifoaming agent, water, and a flavoring agent.

13. The suspension made by the process of claim 12, wherein the amount of preservative is about 0.1 mg/ml to about 5.0 mg/ml.

14. The suspension made by the process of claim 12, wherein the buffer comprises a citrate buffer.

15. The suspension made by the process of claim 14, wherein the citrate buffer concentration is about 3 mM.

16. The suspension made by the process of claim 12, wherein the suspension agent comprises at least one component selected from silicon dioxide, hydroxypropyl methylcellulose, methylcellulose, microcrystalline cellulose, polyvinylpyrrolidone, xanthan gum, magnesium aluminum silicate, crosslinked polyacrylic acid polymers and combinations thereof.

17. The suspension made by the process of claim 12, wherein the suspension agent is a combination of silicon dioxide and hydroxypropyl methylcellulose.

18. The suspension made by the process of claim 12, wherein the antifoaming agent is simethicone.

19. The suspension made by the process of claim 1, wherein a final concentration of amlodipine benzoate in the suspension is equivalent to about 0.8 mg/ml to about 1.2 mg/ml of amlodipine free base.

* * * * *